(12) United States Patent
Stephan et al.

(10) Patent No.: US 10,804,091 B2
(45) Date of Patent: *Oct. 13, 2020

(54) SINGLE PARTICLE ANALYSIS USING OPTICAL DETECTION

(71) Applicant: PERKINELMER HEALTH SCIENCES CANADA, INC., Woodbridge (CA)

(72) Inventors: Chady Stephan, Brampton (CA); Samad Bazargan, Brampton (CA)

(73) Assignee: PerkinElmer Health Sciences Canada, Inc., Woodbridge (ON) (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/209,140

(22) Filed: Dec. 4, 2018

(65) Prior Publication Data

US 2019/0221417 A1 Jul. 18, 2019

Related U.S. Application Data

(63) Continuation-in-part of application No. 16/146,752, filed on Sep. 28, 2018, now Pat. No. 10,395,912, which is a continuation of application No. 15/597,608, filed on May 17, 2017, now Pat. No. 10,147,592.

(60) Provisional application No. 62/337,997, filed on May 18, 2016, provisional application No. 62/596,812, filed on Dec. 9, 2017.

(51) Int. Cl.
*H01J 49/10* (2006.01)
*H01J 49/00* (2006.01)
*H01J 49/26* (2006.01)
*H01J 49/16* (2006.01)
*G01N 30/72* (2006.01)
*H01J 49/04* (2006.01)

(52) U.S. Cl.
CPC ........ *H01J 49/107* (2013.01); *G01N 30/7273* (2013.01); *H01J 49/045* (2013.01); *H01J 49/049* (2013.01); *H01J 49/167* (2013.01)

(58) Field of Classification Search
CPC ...... H01J 49/107; H01J 49/045; H01J 49/049; H01J 49/167; G01N 30/7273
USPC ................................ 250/281, 282, 283, 288
See application file for complete search history.

(56) References Cited

U.S. PATENT DOCUMENTS 10,395,912 B2 * 8/2019 Stephan ............. G01N 30/7273

* cited by examiner

*Primary Examiner* — Nicole M Ippolito
(74) *Attorney, Agent, or Firm* — Rhodes IP PLC; Christopher R Rhodes

(57) ABSTRACT

Methods and systems of identifying two or more elements in a single individual particle are described. In some examples, an optical emission from each of an ionized first element and an ionized second element can simultaneously be detected to identify at least a first element in a particle from a plurality of particles using the optical emission from the ionized first element, and to identify at least a second element in the particle from the plurality of particles using the optical emission from the second ionized element. The identified first element and the identified second element can be used to identify a source of the particle from a plurality of particles.

20 Claims, 16 Drawing Sheets

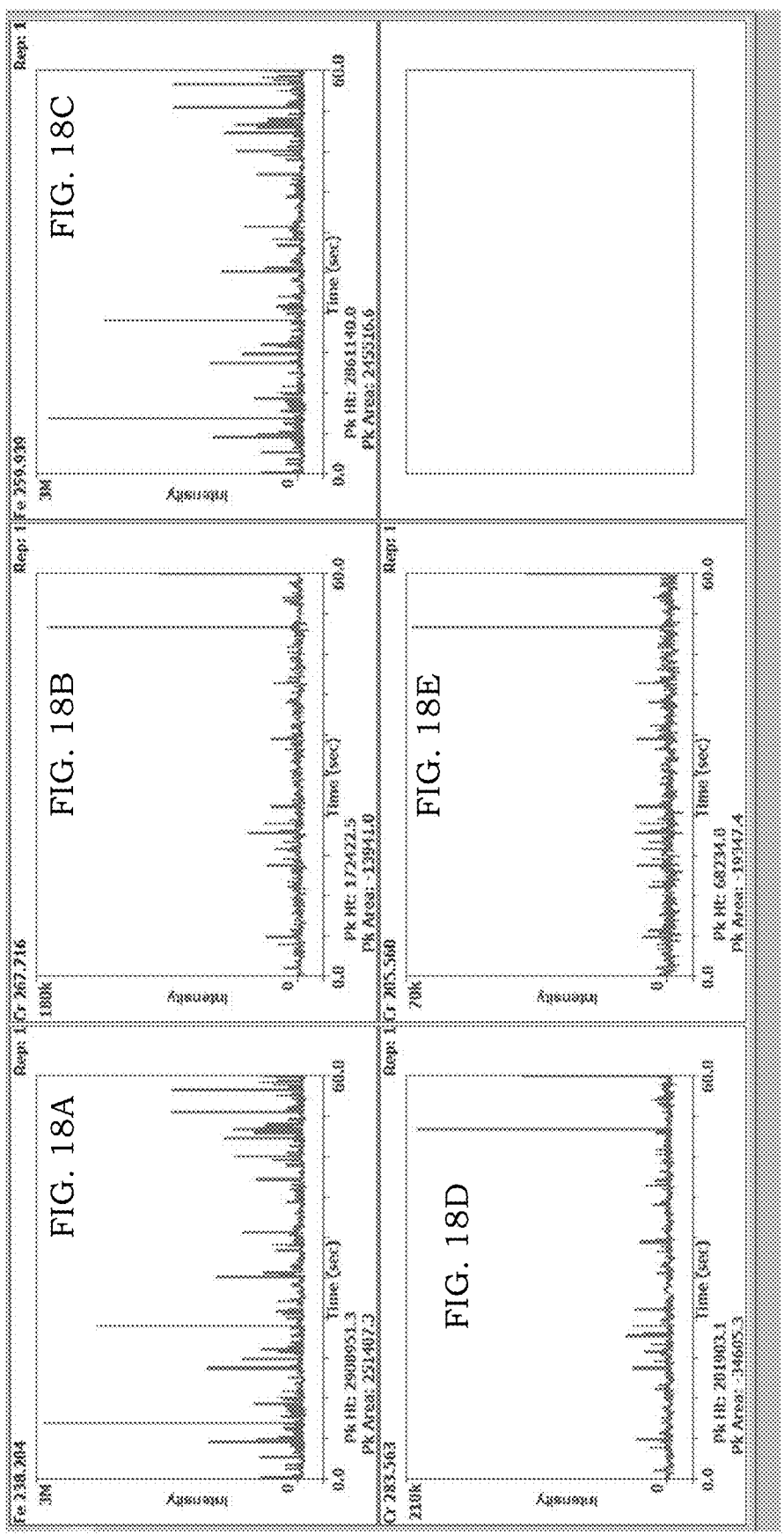

SINGLE PARTICLE ANALYSIS USING OPTICAL DETECTION

PRIORITY APPLICATION

This application is related to, and claims priority to and the benefit of, U.S. Provisional Application No. 62/596,812 filed on Dec. 9, 2017, the entire disclosure of which is hereby incorporated herein by reference for all purposes. This application is a continuation-in-part of U.S. application Ser. No. 16/146,752 filed on Sep. 28, 2018, which claims priority to U.S. application Ser. No. 15/597,608 filed on May 17, 2017.

TECHNOLOGICAL FIELD

Certain configurations described herein are directed to analysis of single particles. More particularly, certain examples are described of single particle analysis using inductively coupled plasma optical detection.

BACKGROUND

It is often desirable to measure particulate matter in ambient environments. Even though the particulate matter may be analyzed, an origin of the particulate matter is not necessarily identifiable in all instances.

SUMMARY

Certain aspect, configurations, embodiments, examples and illustrations are described of methods and systems that can be used to identify one, two or more elements in a particle. The identified elements can then be used to identify a source of the particle if desired.

In some examples, a comprises simultaneously detecting an optical emission from each of an ionized first element and an ionized second element to identify at least a first element in a particle from a plurality of particles using the optical emission from the ionized first element, and to identify at least a second element in the particle from the plurality of particles using the optical emission from the second ionized element. The method may further comprise using the identified first element and the identified second element to identify a source of the particle from a plurality of particles. If desired, three, four or more elements within the individual particle can be identified and used to determine a source of the particle.

In certain examples, the method comprises quantifying an amount of each of the first element and the second element in the particle. In some examples, the method comprises simultaneously detecting an optical emission from an ionized third element to identify a third element in the particle using the optical emission from the ionized third element and identifying the source of the particle using the identified first, second and third elements. For example, the method may also comprise quantifying an amount of each of the first element, the second element and the third element in the particle. If desired, one or more clustering techniques for separating particles from one source versus another source due to their different elemental compositions can be performed.

In some examples, the method may comprise sampling air comprising the particle and providing the sampled air to an ionization device to ionize the first element and the second element in the sampled air.

In other examples, the method may comprise sampling a hydrocarbon fluid comprising the particle and providing the sampled hydrocarbon fluid to an ionization device to ionize the first element and the second element in the sampled hydrocarbon fluid. In some embodiments, the method may comprise quantifying an amount of each of the first element and the second element in the particle and determining a vehicle site exhibiting wear using the quantified amount of the first element and the second element. In other instances, the method may comprise quantifying an amount of each of the first element and the second element in the particle and determining if the hydrocarbon fluid needs to be replaced using the quantified amount of the first element and the second element.

In certain embodiments, the method comprises simultaneously detecting an optical emission from each ionized element from all elements in the particle to identify all elements in the particle. In other examples, the method may comprise quantifying each of the identified elements in the particle and determining a source of the particle using the quantified elements.

In some examples, the method comprises configuring the particle as a nanoparticle. In certain examples, the method comprises identifying the source of the nanoparticle using the identified first element and the identified second element.

In some embodiments, the method may comprise ionizing the particle to provide the ionized first element and the ionized second element. In certain examples, the method comprises ionizing step comprises introducing the particle into an ionization source. In other examples, the method comprises introducing the particle into the ionization source using a spray chamber or a gas exchange device. In some embodiments, the method comprises configuring the ionization source as one of an inductively coupled plasma, a capacitively coupled plasma, a glow discharge, an arc or a spark.

In some examples, the method comprises sampling a fluid comprising the particle, wherein the fluid is sampled in an inline process to monitor a state of the fluid by periodically sampling the fluid, identifying the first element and the second element in the sampled fluid using the optical emissions from the first ionized element and the second ionized element, and quantifying an amount of each of the first element and the second element in the sampled fluid to determine a source of particle in the inline process. In certain embodiments, the method comprises sampling a gas comprising the plurality of particles. In other embodiments, the method comprises sampling a gas used in a semiconductor manufacturing process. In some embodiments, each of the first element and the second element are inorganic elements.

In another aspect, a system for detecting elemental species present in a particle of a plurality of particles is described. In some examples, the system comprises a sample introduction device configured to provide an individual particle from the plurality of particles, wherein the provided individual particle comprises an average diameter of about 100 nm to about 100 microns. The system may further comprise an ionization device fluidically coupled to the sample introduction device and configured to ionize elemental species present in the provided individual particle. The system may further comprise an optical detector configured to simultaneously detect an optical response from each of the ionized elemental species from the provided individual particle.

In certain embodiments, the sample introduction device is configured as a spray chamber or a gas exchange device. In other embodiments, the sample introduction device is configured to directly inject the individual particle into the ionization device. In some examples, the optical detector comprises an optical spectrometer. In certain examples, the system comprises a processor electrically coupled to the optical detector and configured to quantify an amount of each element from a detected optical emission from each of the ionized elemental species, e.g., the processor can be configured to execute instructions for quantifying an amount of each element from a detected optical emission from each of the ionized elemental species. In some examples, the processor is further configured to determine a source of the particle using the quantified amount of each element, e.g., can be configured to execute instructions to determine a source of the particle using the quantified amount of each element.

In certain examples, the sample introduction device is configured to provide an individual particle to the ionization device. In other examples, the sample introduction device is configured to provide a hydrocarbon fluid comprising the particle to the ionization device. In some embodiments, the processor is configured to determine a wear location site using the quantified amount of the each of the elements in the particle.

In some examples, the sample introduction device is configured to periodically sample a fluid present in an inline process and provide the sampled fluid to the ionization device.

In other examples, the sample introduction device is configured to provide an air sample comprising the particle to the ionization device. In some embodiments, the sample introduction device is configured to automatically sample an air space of a building and provide the sampled air space to the ionization device.

In certain embodiments, the optical detector comprises at least one grating to spatially separate each optical emission wavelength from other optical emission wavelengths to permit simultaneous detection of each of the ionized elemental species.

In some configurations, the ionization device comprises a torch and an induction device configured to sustain an inductively coupled plasma within the torch. In some examples, the induction device is configured as an induction coil, a plate electrode or a radially finned induction device.

In some examples, the system may comprise a second ionization device fluidically coupled to the sample introduction device, the second ionization device and the ionization device configured to operate in parallel. The system may also comprise a second detector fluidically coupled to the second ionization device, the second detector configured to simultaneously detect optical emissions from each of the ionized elemental species present in the second ionization device. The system may further comprise a sampling device fluidically coupled to the ionization device in a first state and fluidically coupled to the second ionization device in a second state. The system may further comprise a processor electrically coupled to the optical detector and configured to execute instructions for quantifying an amount of each element from a detected optical absorption from each of the ionized elemental species, wherein the processor is further configured to determine a source of the particle using the quantified amount of each element.

In certain embodiments, a method of identifying a source of a material comprises simultaneously detecting an optical emission from each of an ionized first element and an ionized second element to quantify at least a first element in a particle of the material using the optical emission from the ionized first element and to quantify at least a second element in the particle of the material using the optical emission from the second ionized element, and using the quantified first element and the quantified second element to identify the source of the material.

Additional aspects, embodiments, configurations and examples are described in more detail below.

BRIEF DESCRIPTION OF THE SEVERAL VIEWS OF THE DRAWINGS

Certain illustrations of the technology described herein are described in more detail below with reference to the drawings in which:

FIGS. 18A, 18B, 18C, 18D and 18E are graphs showing the signal intensity as a function of time for iron and chromium, in accordance with some embodiments.

Figure 1:
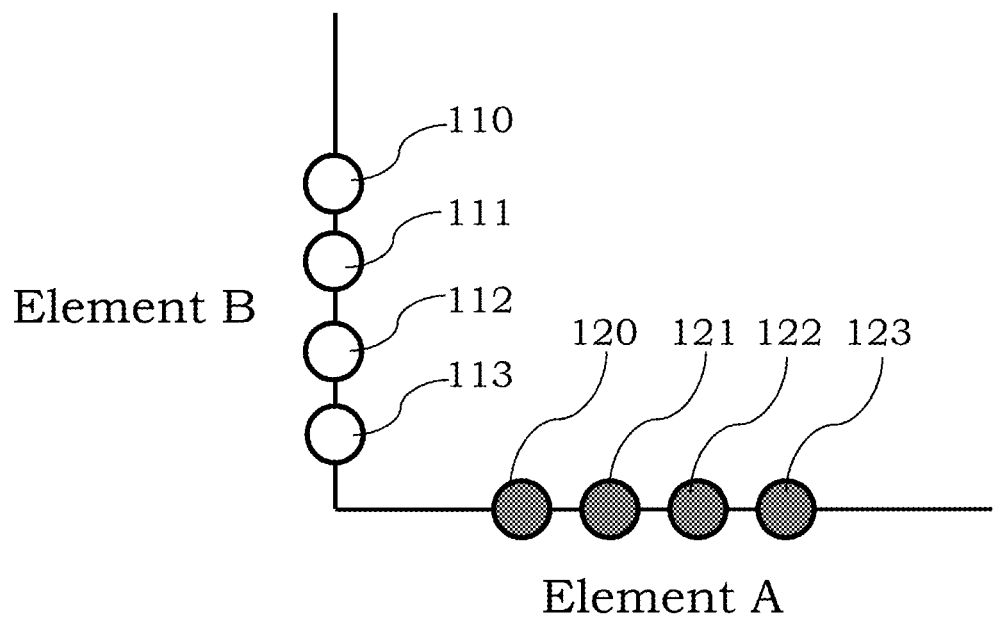
FIG. 1 is an illustration showing two elemental species present in different individual particles, in accordance with certain examples.

It will be recognized by the person of ordinary skill in the art, given the benefit of this disclosure, that the representations in the drawings are provided merely for illustration purposes. The exact optical response, dimensions of the components and configuration of the systems may vary depending on the intended use of the methods and systems.

DETAILED DESCRIPTION

Certain illustrations of methods, systems and devices are provided below to facilitate a better understanding of the technology described herein. In some instances, reference is made to a single particle being analyzed for its elemental content or some portion thereof. It will be recognized by the person of ordinary skill in the art, given the benefit of this disclosure, that more than one particle can be analyzed, and the reference to single particle does not mean that only a single particle is or can be analyzed using the methods, systems and devices described herein.

In some examples, the methods, systems and devices described herein can be used to detect one, two or more than two elements within a single individual particle. The single particle may be present as an individual particle or a stable aggregate or association or system of particles. Without wishing to be bound by this particular illustration, by detecting two or more elements within a single particle it can be possible to determine a source of the particle. For example, a single particle comprising copper and zinc can be linked to a brass material, a single particle comprising iron and chromium can be linked to a steel material, a single particle comprising two particular elements can be linked to a wear site in an engine, a single particle comprising two particular elements can be linked to a source of specific air borne particles, a single particle comprising two or three particular elements can be linked to gun powder, etc. In some examples, the exact size of the single particle, e.g., an average particle diameter, may vary from about 0.5 microns up to about 100 microns, more particularly about 0.5 microns to about 50 microns or about 0.5 microns to about 10 microns, though smaller or larger particles can also be analyzed using the methods and systems described herein. If desired, both the identity of the element(s) in a single particle and an amount of the element(s) in the single particle can be determined.

In certain embodiments, the methods, systems and devices described herein can be used, for example, to determine a source of the analyzed particles. Referring to FIG. 1, an illustration is shown where an element A and an element B are present independently in separate particles. Optical signals 110-113, e.g., optical emission or optical absorption signals, from first particles comprising element A and optical signals 120-123 from second particles comprising element B are shown. As each particle (or the ionized products from each particle) is provided to an optical detector, the identity and amount of each of element A and element B can be determined. Because any one particle comprises only one of the elements (A or B), only a single element is detected for any one particle. As noted in more detail below, each of elements A and B can emit or absorb light at a characteristic wavelength that can be used to determine the identity and amount of each element present in the particle.

Figure 2:
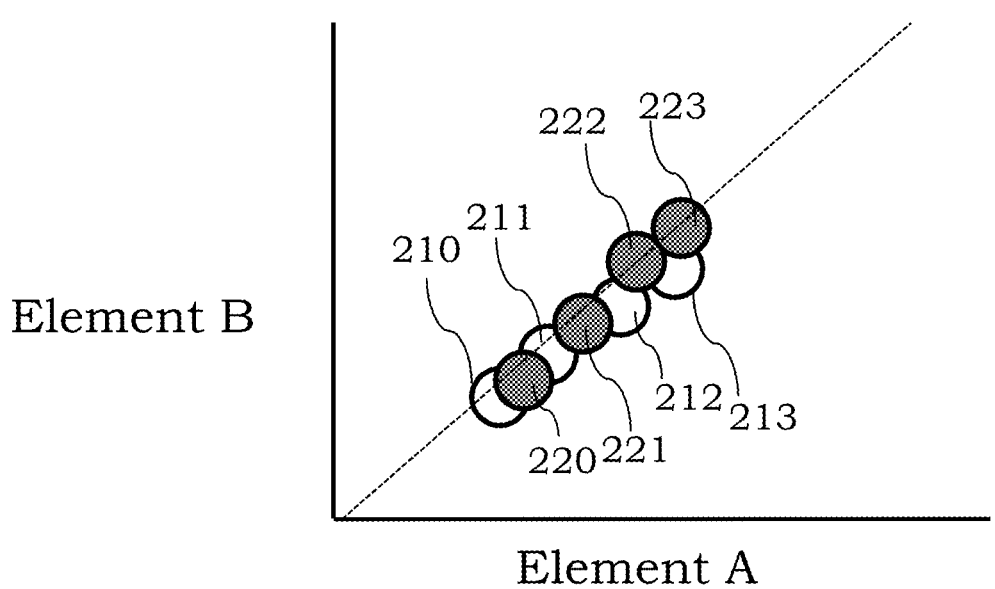
FIG. 2 is an illustration showing two elemental species present together in individual particles, in accordance with certain examples.

In certain examples, it may be desirable to detect the presence of two or more elements in a single particle. An illustration is shown in FIG. 2 where the particles provide optical signals 210-213 and 220-223. As each particle is introduced into an ionization source, the elements A and B are atomized and/or ionized and provided to a downstream optical detector. Because both elements are present in a single particle, both elements A and B are simultaneously detected by the optical detector. The illustration shown in FIG. 2 assumes the elements A and B are present in a fixed ratio in each of the individual particles and a fixed response is observed for the elements in any one particle.

Figure 3:
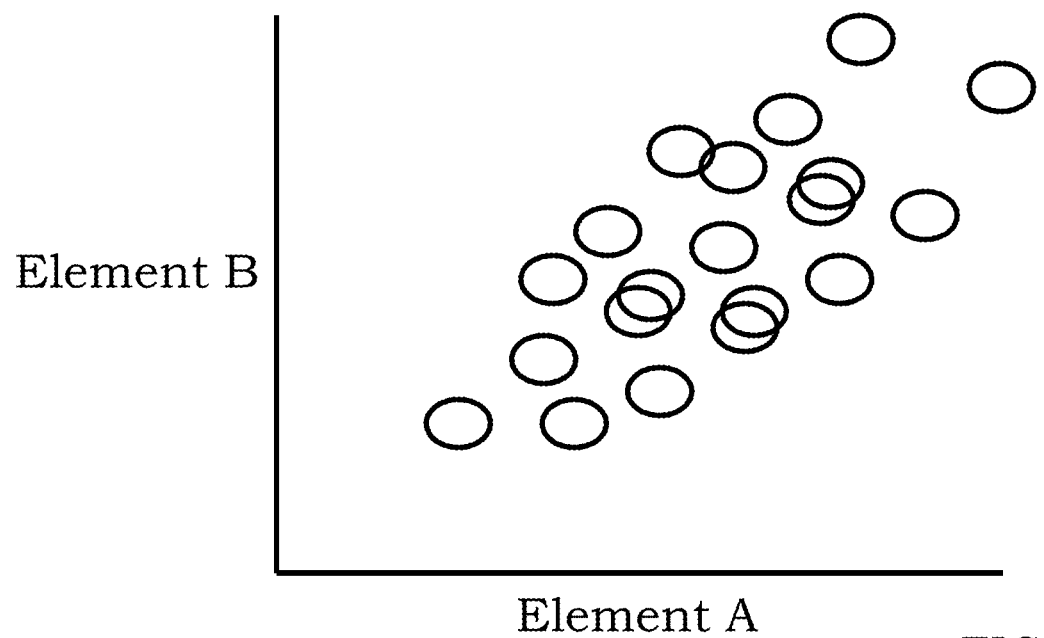
FIG. 3 is another illustration showing two elemental species present together in individual particles, in accordance with certain embodiments.
Figure 4:
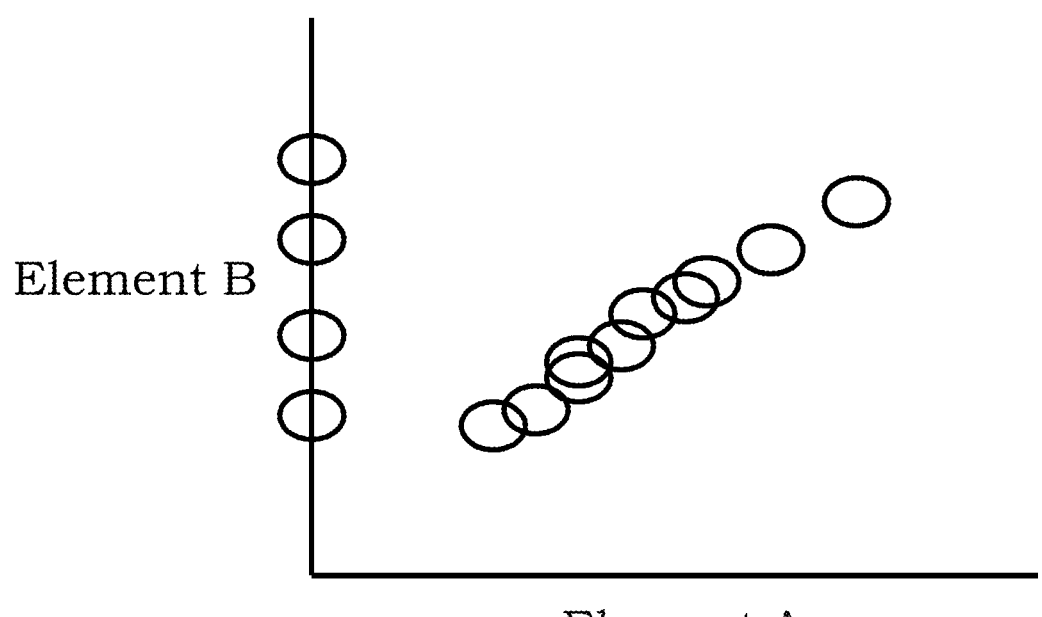
FIG. 4 is an additional illustration showing two elemental species present together in individual particles and individual particles where only one of the elemental species is present by itself, in accordance with certain examples.

In some examples, the elements A and B may be present at variable ratios in different particles where some particles have higher amounts of one element than other particles. An illustration of a possible optical response is shown in FIG. 3 where elements A and B exist together in a variable ratio in individual particles. Different amounts of elements A and B may be detected in different individual particles, which can result in spreading out of the optical signals. In some instances, certain individual particles may comprise only a single element whereas other individual particles may comprise two or more elements. Referring to FIG. 4, an illustration of the optical response where certain individual particles only comprise element B and other individual particles comprise elements A and B. As each individual particle is provided to the ionization source, the elements may be ionized and provided to a downstream optical detector so that elements A and B can be simultaneously detected. Some particles may lack element A entirely, whereas other particles may comprise both elements A and B. In the illustration of FIG. 4, elements A and B are generally present in a fixed or constant ratio, though they could be present in a variable ratio as well.

Figure 5:
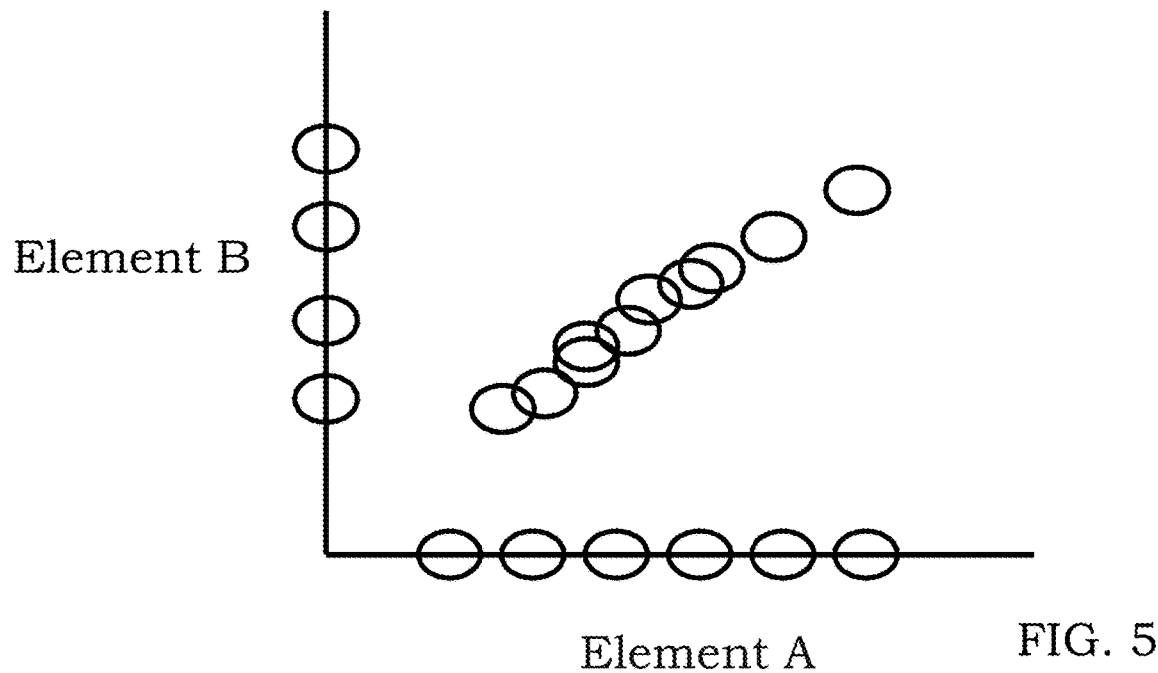
FIG. 5 is an additional illustration showing two elemental species present together in individual particles and individual particles where each of the elemental species is present by itself, in accordance with certain examples.

In other instances, elements A and B may be present in individual particles together but there may also be particles which only comprise one of element A and one of element B. In such instances, an optical response similar to that shown in FIG. 5 may be encountered. In this illustration, some particles only comprise element A (and provide no optical response when element B is being detected), some particles only comprise element B (and provide no optical response when element A is being detected), and some particles comprise both elements A and element B (and provide an optical response when both elements A and B are simultaneously being detected).

Figure 6:
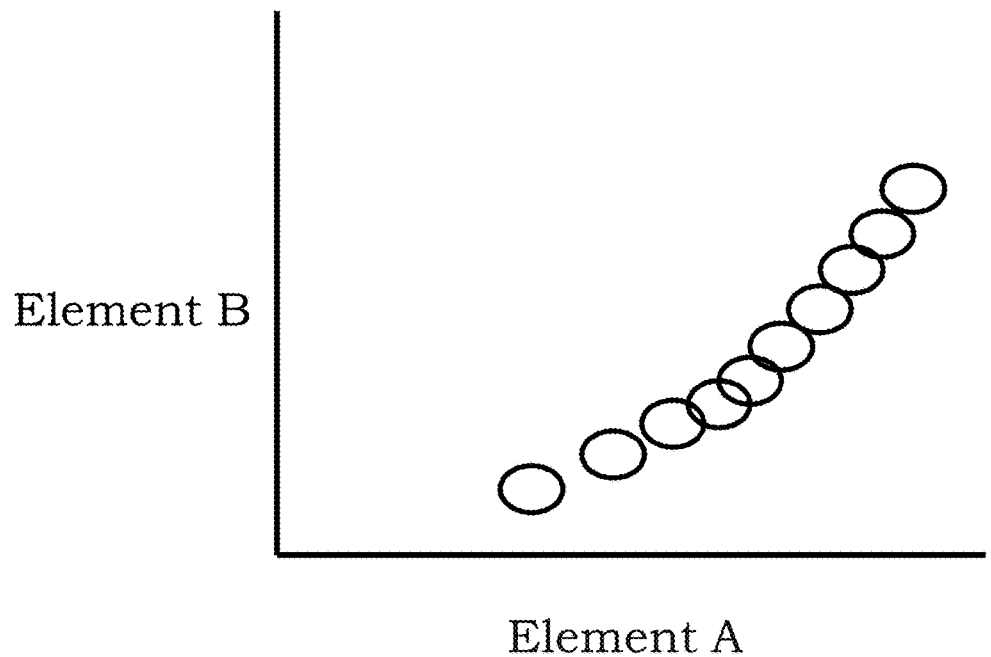
FIG. 6 is another illustration showing two elemental species present together in individual particles as a core shell scenario, in accordance with certain embodiments.

In some examples, the exact nature of the particles where two elements are present together may vary. In some examples, the elements A and B may be bound or coordinated to different groups of the particle, whereas in other instances one or more of the elements A or B can be present in a different structure of the particle that forms a portion of the particle. For example, one of the elements may be present in a core of a core shell particle configuration and the other element can be present in the shell of a core shell particle configuration. An illustration is shown in FIG. 6 where elements A and B exist together with element A being in the core of the particle (with variable core size) and element B being in the shell of the particle (with fixed shell size). An illustration of a possible optical response is shown, which shows that the presence of the core-shell configuration can provide a different response than when the elements are present in a common structural component of a single particle (see FIG. 2).

Figure 7:
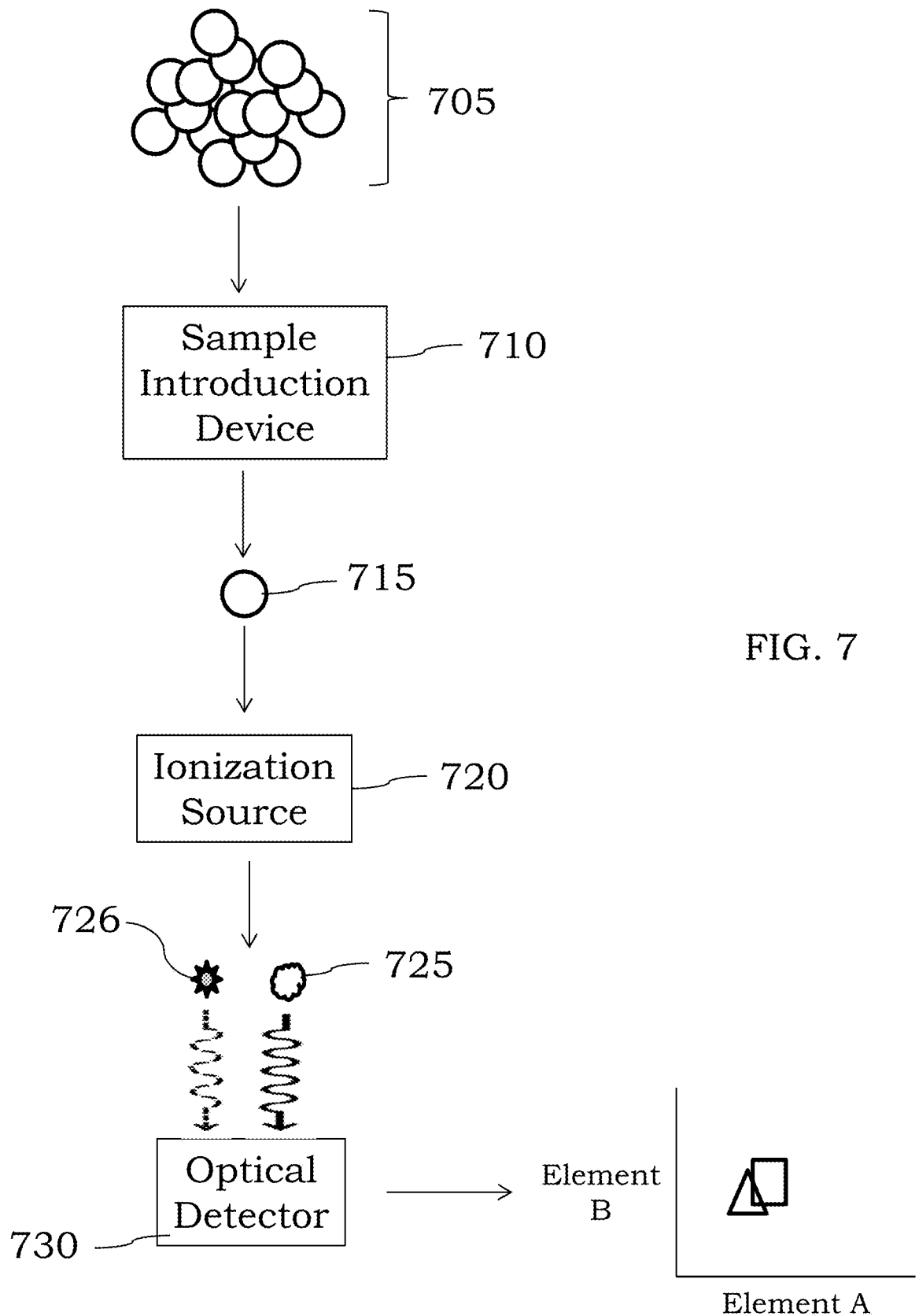
FIG. 7 is an illustration of a process to detect two or more elemental species present in an individual particle, in accordance with certain examples.

In certain examples, two or more elements within a single particle can simultaneously be detected using an optical response or signal from each of an ionized first element and an ionized second element to identify at least the first element in a particle and to identify at least the second element in the particle. The identified first element and the identified second element can be used to identify a source of the particle from a plurality of particles. If desired, an amount of each of the ionized first element and the ionized second element can also be determined to quantitate how much of each of the first element and the second element is present in the individual particle. A third element, fourth element, etc. can also be identified and/or quantified in the individual particle. A generalized illustration of a process for identifying at least a first element and at least a second element is shown in FIG. 7. A plurality of individual particles (collectively 705) can be introduced into a sample introduction device 710 to select or provide an individual particle 715 from the plurality of individual particles 705. The provided individual particle 715 can then be provided to an ionization source 720 to ionize the elemental species in the provided individual particle 715. While not shown, each individual particle of the plurality of individual particles can be provided to the ionization source 720 to detect the first element and the second element in each provided individual particle, e.g., sequentially. Depending on the exact ionization source selected, the organic elements present in the individual particle 715 are atomized/ionized and generally do not emit light (or absorb light) at similar wavelengths as any ionized inorganic elemental species. After ionization of the individual particle 715 in the ionization source 720, the elemental species 725, 726 can be provided to an optical detector 730 for detection, or light emitted from or absorbed by the species 725, 726 can be detected by the optical detector 730. The optical detector 730 can be configured to simultaneously detect an optical response for each of the elemental species 725, 726 as shown in the graph in FIG. 7. The detected optical signals for each of elements A and B in each of the individual particles from the plurality of particles 705 can be used to determine a source of the particles. In some examples, the exact optical response or optical signal from the first element and second element can vary. As noted below, in some instances, an optical emission from each of the first element and the second element can simultaneously be detected and used to determine the identity of the elements and how much of each element is present in each individual particle. While the exact emission wavelength varies from element to element and certain elements can emit light at more than a single wavelength, different emission wavelengths can be monitored so that minimal spectral emission wavelength overlap is observed during the simultaneous detection of the two or more elements. In other instances, light absorption by the first element and second element can be used to identify the elements present and/or the amount of the elements that are present in the individual particle.

In some examples, the exact sample introduction device used may depend, at least in part, on the environment of the particles. For example, where the particles are present in a liquid sample the sample introduction device may comprise or use a nebulizer, an injector, capillary tubing, etc. Where a nebulizer is used, the nebulizer can take many forms including crossflow nebulizers, concentric nebulizers and microflow nebulizers. The nebulizer can be used by itself or in combination with one or more spray chambers as noted below. Where injectors are used, the injector may take the form of a needle, capillary or other tubing with a small orifice. In some examples, the sample introduction device can be configured to provide individual particles from a plurality or particles introduced into the sample introduction device. For example, a spray chamber similar to an Asperon™ spray chamber commercially available from PerkinElmer Health Sciences, Inc. (Waltham, Mass.) or other suitable spray chambers can be used. The dimensions and/or configuration of the spray chamber can be selected to permit particles as large as 100 microns to be provided from the sample introduction device to the downstream ionization source.

Figure 8:
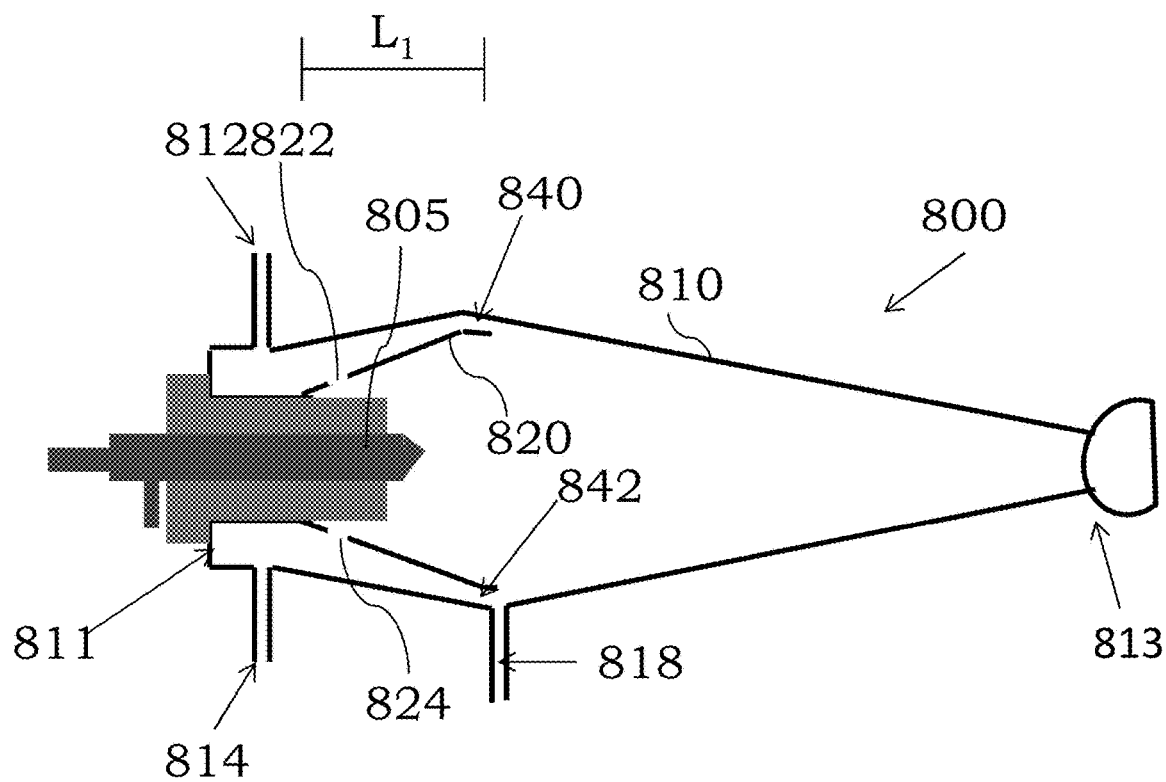
FIG. 8 is an illustration of one type of a sample introduction device that can be used with particles present in a liquid, in accordance with certain examples.

One illustration of a spray chamber is shown in FIG. 8. The spray chamber 800 generally comprises an outer chamber or tube 810 and an inner chamber or tube 810. The outer chamber 810 comprises dual makeup gas inlets 812, 814 and a drain 818. The makeup gas inlets 812, 814 are typically fluidically coupled to a common gas source, though different gases could be used if desired. While not required, the makeup gas inlets 812, 814 are shown as being positioned adjacent to an inlet end 811, though they could instead be positioned centrally or toward an outlet end 813. The inner chamber or tube 820 is positioned adjacent to a nebulizer tip 805 and may comprise two or more microchannels 822, 824 configured to provide a makeup gas flow to reduce or prevent particle droplets from back flowing and/or depositing on the inner tube 820. The configuration and positioning of the inner tube 820 provides laminar flow at areas 840, 842 which acts to shield inner surfaces of the outer chamber 810 from any droplet deposition. The tangential gas flow provided by way of gas introduction into the spray chamber 800 through the inlets 812, 814 acts to select particles of a certain size range. The microchannels 822, 824 in the inner tube 820 also are designed to permit the gas flows from the makeup gas inlets 812, 814 to shield the surfaces of the inner chamber or tube 820 from droplet deposition. In certain examples, the microchannels 822, 824 can be configured in a similar manner, e.g., have the same size and/or diameter, whereas in other configurations the microchannels 822, 824 may be sized or arranged differently. In some instances, at least two, three, four, five or more separate microchannels can be present in the inner chamber or tube 820. The exact size, form and shape of the microchannels may vary and each microchannel need not have the same size, form or shape. In some examples, different diameter microchannels may exist at different radial planes along a longitudinal axis L1 of the inner tube to provide a desired shielding effect. Illustrative spray chambers are described, for example, in U.S. patent application Ser. No. 15/597,608 filed on May 17, 2017, the entire disclosure of which is hereby incorporated herein by reference for all purposes.

In certain embodiments, the exact dimensions of the spray chamber 800 may vary. In certain configurations, a longitudinal length from the nebulizer tip 805 to the end of the spray chamber 800 may be about 10 cm to about 15 cm, e.g., about 12 or 13 cm. The diameter of the outer tube 810 may vary from about 1 cm to about 5 cm, e.g., about 3 cm or 4 cm. The largest diameter of the inner tube 820 may vary from about 0.5 cm to about 4 cm, and the distance between outer surfaces of the inner tube 820 and inner surfaces of the outer tube 810 can be selected to provide a desired laminar flow rate, e.g., the distance may be about 0.1 cm to about 0.75 cm. In certain examples, the inner tube 820 is shown as having a generally increasing internal diameter along the longitudinal axis of the outer chamber 810, but this dimensional change is not required. Some portion of the inner tube 810 may be "flat" or generally parallel with the longitudinal axis L1 to enhance the laminar flow, or in an alternative configuration, some portion of the inner tube 820 may generally be parallel to the surface of the outer tube 810, at least for some length, to enhance laminar flow. The inner diameter of the outer chamber increases from the inlet end 811 toward the outlet end 813 up to a point and then decreases toward the outlet end 813 such that the inner diameter of the outer chamber 810 is smaller at the outlet end 813 than at the inlet end 811. If desired, the inner diameter of the outer chamber 810 may remain constant from the inlet end 811 toward the outlet end 813 or may increase from the inlet end 811 toward the outlet end 813. If desired, two or more different spray chambers which are the same or different can be fluidically coupled to each other to assist in selection of individual particles from a plurality of particles.

Figure 9:
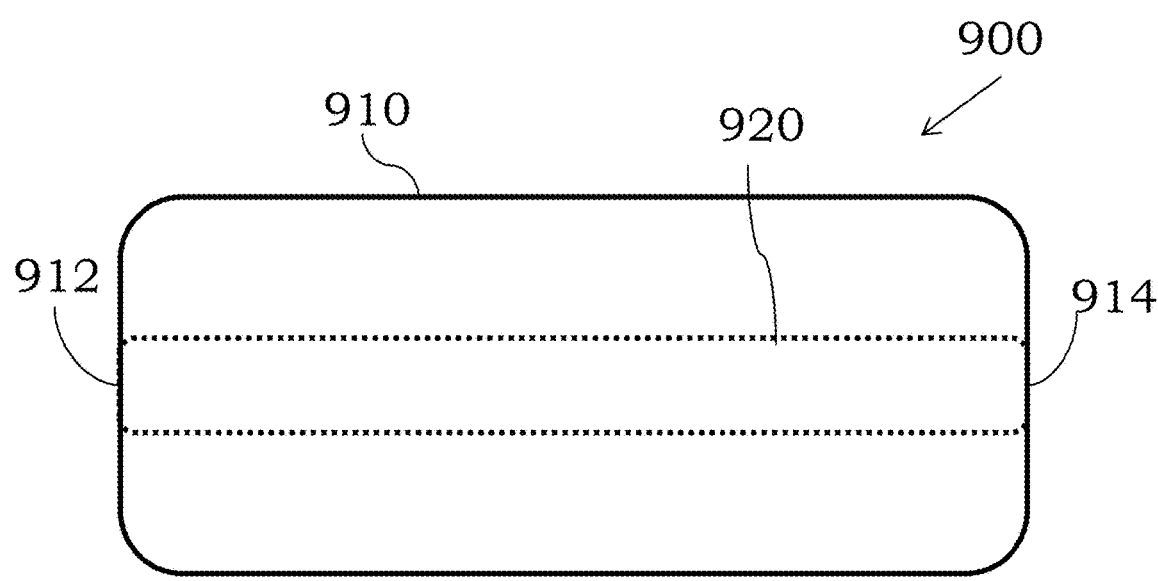
FIG. 9 is an illustration of one type of a sample introduction device that can be used with particles present in a gas, in accordance with certain examples.

In some examples, it may be desirable to sample an air space with particles present in gaseous form. For example, in many industrial settings, it may be desirable to keep a level of certain air borne particles below a threshold level to ensure worker safety and/or increase air quality. The air space can be sampled to extract some of the gaseous particles to test whether or not certain types of particles are present. For example, particulate matter can be analyzed to determine selected particles of a desired size, e.g., similar to $PM_{10}$, $PM_{2.5}$ and $PM_1$ monitoring, and determine whether or not any particularly hazardous particles are present in the air sample. In some examples where gaseous particles are analyzed, a gas exchange device (GED) may be present as or part of the sample introduction device. The exact form of the gas exchange device used may vary based on the air sampled and the desired output from the gas exchange device. In one example, a gas exchange device may comprise two or more tubes or chambers where an inner tube or chamber comprises a porous membrane or pores of a desired size. A simplified gas exchange device 900 is shown in FIG. 9 as comprising an outer tube 910 and an inner tube 920. A sampled gas comprising gaseous particles can be introduced into the inner tube 920 through an inlet 912. A gas such as argon or other inert gases may be introduced into the outer tube 910 through an inlet (not shown) and used as a sweep gas. Pressure differences between the sweep gas and the sampled gas can act to permit the sweep gas to diffuse into the inner tube 920 and permit non-particle species to diffuse from the inner tube 920 into the outer tube 910. The particles within the air sample are generally large (compared to the size of ambient gases in the sampled air) and diffuse to little or no degree through the porous membrane of the inner tube 920. The sweep gas flows into the inner tube 910 and can be used to carry the gaseous particles in the inner tube 920 to a downstream ionization source through an outlet 914 of the gas exchange device 900. If desired, a gas exchange device can be coupled to a different sample introduction device such as an injector, capillary tube, spray chamber, another GED, etc. The pore size present in the inner tube 920 can vary depending on the desired particle size to be used and may act to filter out smaller particles from the air sample if desired. While not shown, an additional outlet may be present and fluidically coupled to the outer tube 910 to permit the sweep gas and non-particulate material extracted from the sampled air to exit from the outer tube 910.

In some embodiments, the ionization source 720 may take many different forms and is generally effective to ionize the elemental species present in each individual particle. In some examples, the ionization source may be a high temperature ionization source, e.g., one with an average temperature of about 4000 Kelvin or more, such as, for example, a direct current plasma, an inductively coupled plasma, an arc, a spark or other high temperature ionization sources. The exact ionization source used may vary depending on the particular elements and/or particles to be analyzed, and illustrative ionization sources include those which can atomize and/or ionize the elemental species to be detected, e.g., those ionization sources which can atomize and/or ionize metals, metalloids and other inorganic species or organic species.

Figure 10:
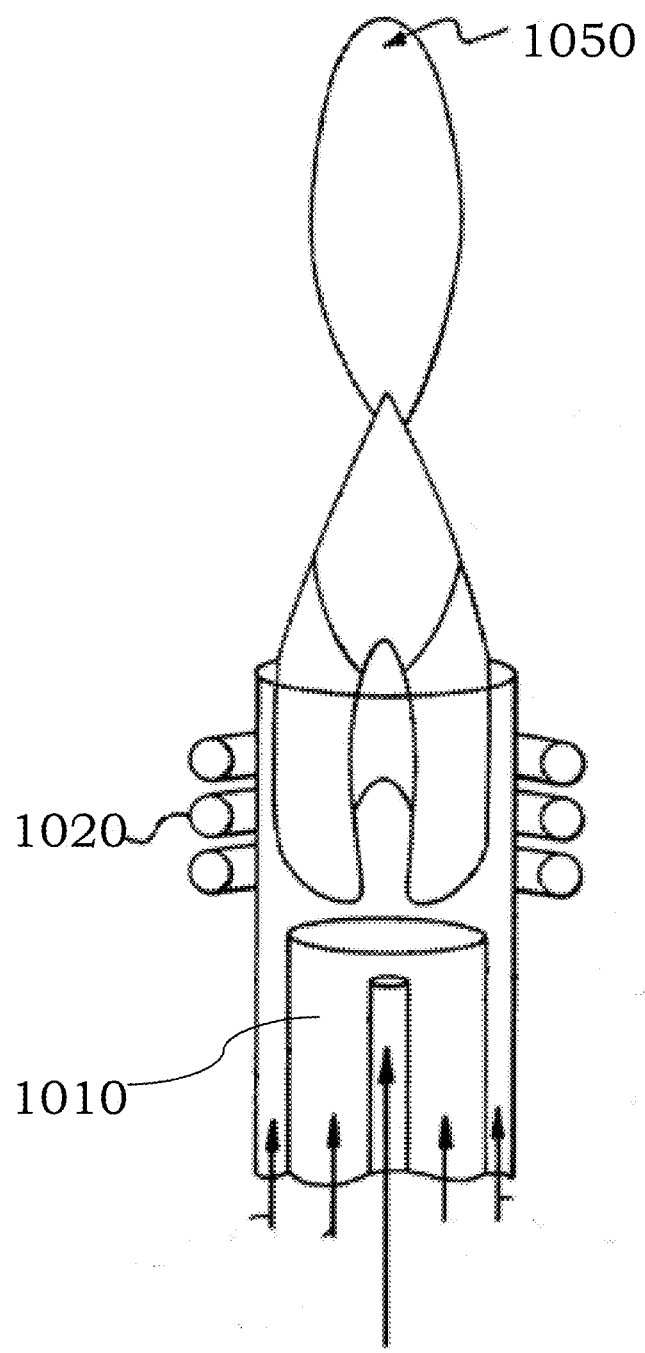
FIG. 10 is an illustration of one type of ionization source, in accordance with certain examples.
Figure 11:
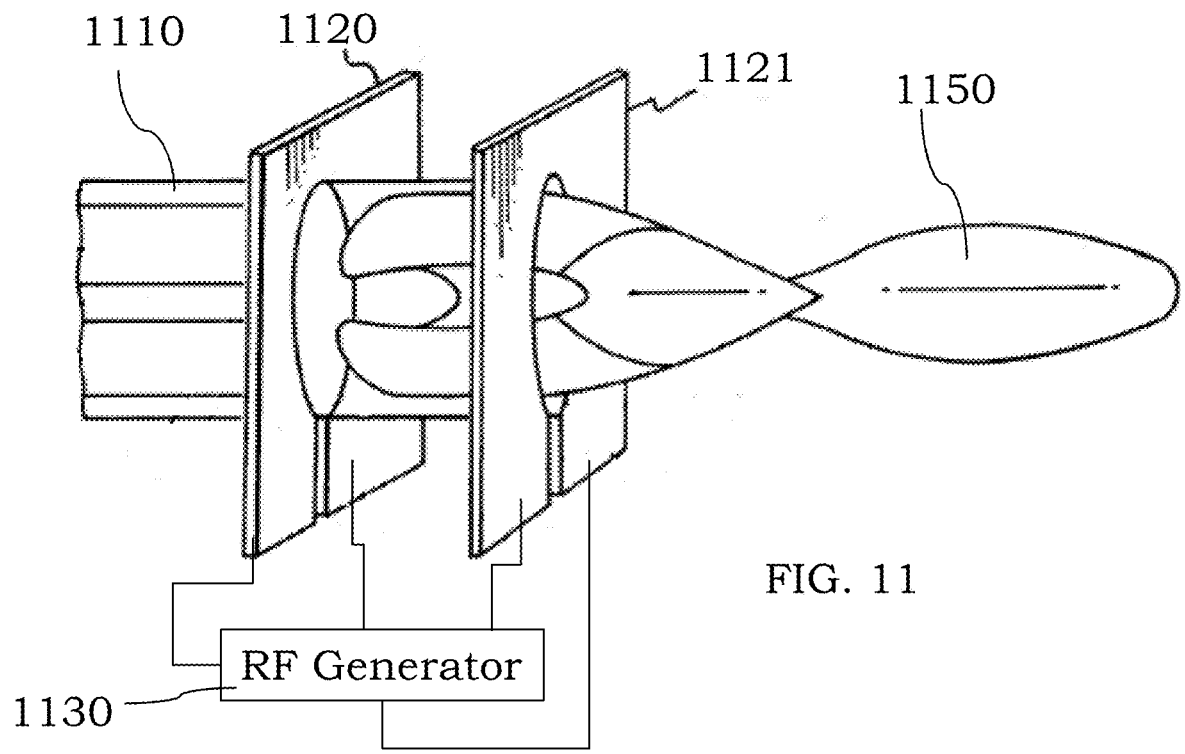
FIG. 11 is an illustration of another type of ionization source, in accordance with certain examples.
Figure 12:
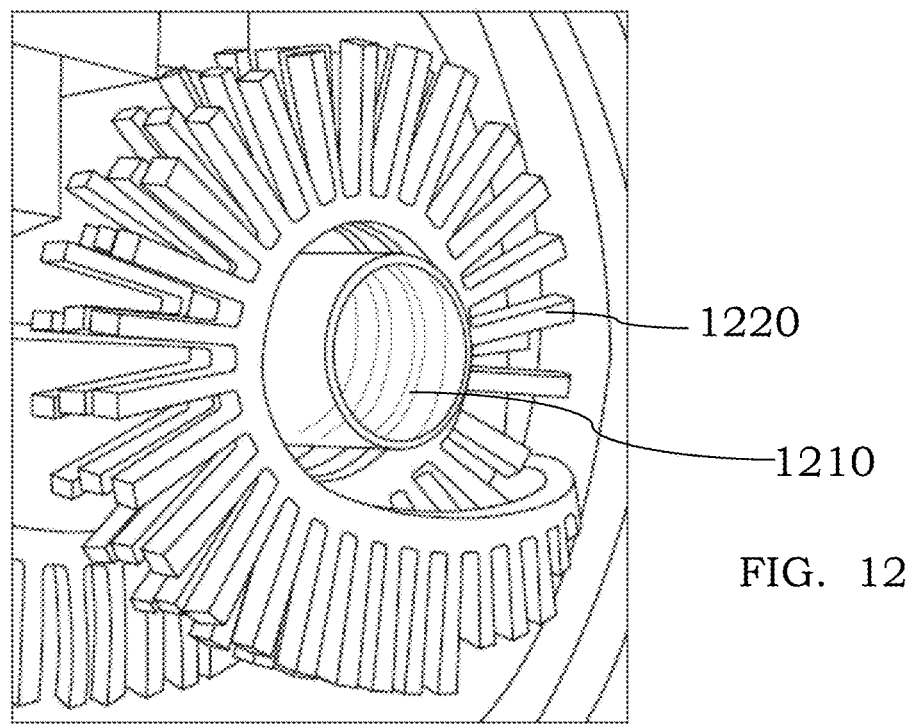
FIG. 12 is an additional illustration of an ionization source, in accordance with certain examples.

In certain examples, the ionization source may comprise one or more torches and one or more induction devices. Certain components of an ionization source are shown in FIGS. 10-12. Illustrative induction devices and torches are described, for example, in U.S. Pat. Nos. 9,433,073 and 9,360,403, the entire disclosure of which is hereby incorporated herein by reference for all purposes. Referring to FIG. 10, a device comprising a torch 1010 in combination with an induction coil 1020 is shown. The induction coil 1020 is typically electrically coupled to a radio frequency generator (not shown) to provide radio frequency energy into the torch 1010 and sustain an inductively coupled plasma 1050 within some portion of the torch 1010. A sample introduction device (not shown) can be used to introduce individual particles into the plasma 1050 to ionize and/or atomize the elemental species present in the individual particle. The ionized and/or atomized elemental species may be detected within the torch using axial or radial detection or can be provided to a downstream chamber or other device for detection. In some instances, optical emissions from each of the two or more elemental species within the torch 1010 can be simultaneously detected using a detector optically coupled to the torch 1010.

In an alternative configuration, the induction coil 1020 in FIG. 10 could be replaced with one or more plate electrodes. For example and referring to FIG. 11, a first plate electrode 1120 and a second plate electrode 1121 are shown as comprising an aperture that can receive a torch 1110. For example, the torch 1110 can be placed within some region of an induction device comprising plate electrodes 1120, 1121. A plasma or other ionization/atomization source 1150 such as, for example, an inductively coupled plasma can be sustained using the torch 1110 and inductive energy from the plates 1120, 1121. A radio frequency generator 1130 is electrically coupled to each of the plates 1120, 1121. If desired, only a single plate electrode could be used instead. A sample introduction device can be used to introduce individual particles into the plasma 1150 to ionize and/or atomize species in the sample. In a typical configuration, a nebulizer is fluidically coupled to a spray chamber to provide liquid sample to the spray chamber. The spray chamber can select and aerosolize individual particle and provide them to the plasma 1150. Alternatively, a gas exchange device can be used to provide individual gaseous particles into the plasma 1150. Two or more elemental species in the introduced individual particle can be ionized or atomized and detected using optical techniques to identify and/or quantitate the elemental species present in the individual particle.

In other configurations, an induction device comprising one or more radial fins could instead be used in methods and systems described herein. Referring to FIG. 12, a device or system may comprise an induction coil 1220 comprising at least one radial fin and a torch 1210. A plasma or other ionization/atomization source (not shown) such as, for example, an inductively coupled plasma can be sustained using the torch 1210 and inductive energy from the radially finned induction device 1220. A radio frequency generator (not shown) can be electrically coupled to the induction device 1220 to provide radio frequency energy into the torch 1210. A sample introduction device (not shown) can be used to introduce individual particles into the torch 1210. Elemental species in the introduced individual particle can be ionized or atomized and detected using optical techniques to identify and/or quantitate the elemental species present in the individual particle. In other instances, one or more capacitive device such as, for example, capacitive coils or capacitive plates can be used in an ionization source. Further two or more induction devices, capacitive devices or other devices which can provide energy into the torch to sustain an atomization/ionization source such as a plasma can also be used.

In certain embodiments, the two or more elemental species present in the individual particle may be detected by measuring an optical signal or response. The exact type of optical signal or response can vary and optical emission or optical absorption are typically used to identify and/or quantify the elemental species. In some examples, a suitable detector which can simultaneously detect two or more wavelengths of light can be used to measure the presence of an optical signal from each of the elemental species. For example, when the individual particle is introduced into an ionization source and is ionized, each elemental species in the particle can emit light as it is excited by energy from the ionization source. The detector can receive the emitted optical signals simultaneously from the different elemental species and can determine an identity of the elemental species based on the emitted wavelength and/or can determine an amount of the identified elemental species using an optical emission intensity. Illustrative detectors include, but are not limited to, a detector comprising one or more complementary metal-oxide-semiconductor (CMOS) devices, a detector comprising one or more charge-coupled devices (CCDs) and other detectors that may comprise individually addressable arrays or pixels that can be used to simultaneously detect two or more light emissions with different wavelengths. If desired, the detector may be configured as a two dimensional detector array which can be used to detect and/or image the various wavelengths of light emitted from the elemental species. In some embodiments, the detector may comprise a photomultiplier tube, gratings, lenses, etc. to be able to detect one, two or more different wavelengths of emitted light.

Figure 13:
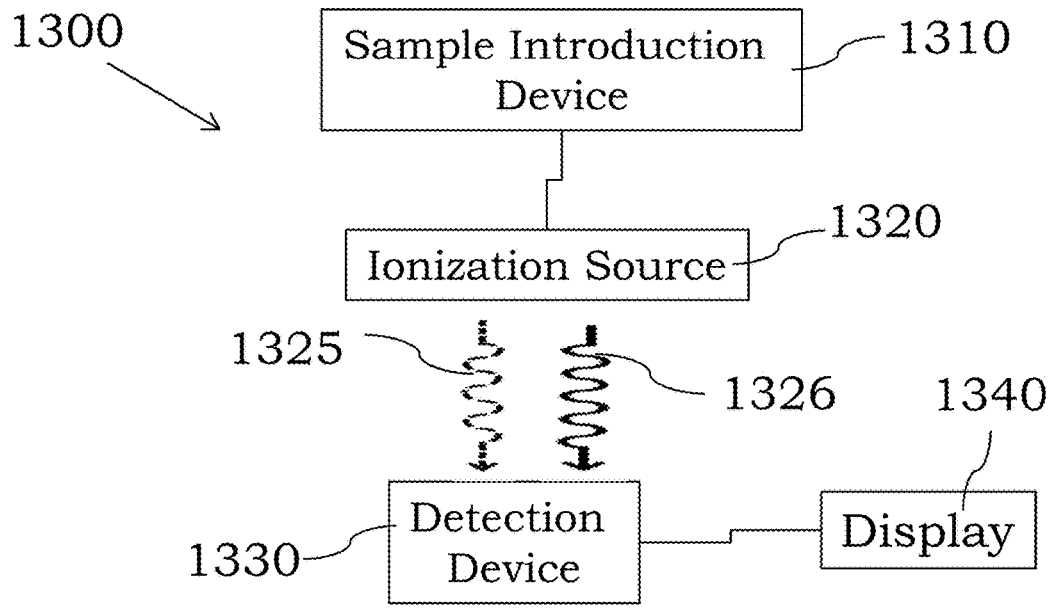
FIG. 13 is an illustration of an optical emission spectrometer, in accordance with certain embodiments.

In certain configurations, the elemental species present in the individual particle can be detected using optical emission spectroscopy (OES). Referring to FIG. 13, an OES device or system 1300 includes a sample introduction device 1310, an ionization source or device 1320 and a detector or detection device 1330. The sample introduction device 1310 may comprise a spray chamber, gas exchange device or may take other forms. The ionization device 1320 may comprise, for example, one or more components as illustrated in FIGS. 10-12 or other devices and components which can provide or sustain an ionization source. The detector or detection device 1330 may take numerous forms and may be any suitable device that may simultaneously detect optical emissions from two or more elemental species, such as optical emissions 1325, 1326. If desired, the detection device 1330 may include suitable optics, such as lenses, mirrors, prisms, windows, band-pass filters, etc. The detection device 1330 may also include gratings, such as echelle gratings, to provide a multi-channel OES device. Gratings such as echelle gratings may allow for simultaneous detection of multiple emission wavelengths. The gratings may be positioned within a monochromator or other suitable device for selection of one or more particular wavelengths to monitor.

In some examples, the OES device 1300 may be configured to implement Fourier transforms to provide simultaneous detection of multiple emission wavelengths. The detection device 1330 may be configured to monitor emission wavelengths over a large wavelength range including, but not limited to, ultraviolet, visible, near and far infrared, etc. The OES device 1300 may further include suitable electronics such as a microprocessor and/or computer and suitable circuitry to provide a desired signal and/or for data acquisition. Suitable additional devices and circuitry are known in the art and may be found, for example, on commercially available OES devices such as Optima 2100DV series, Optima 5000 DV series OES devices or Optima 8000 or 8300 series OES devices commercially available from PerkinElmer Health Sciences, Inc. An optional display 1340, which may be a readout, screen, printer, computer, etc. may be present to monitor detection of the elemental species. The OES devices may further include autosamplers, such as AS90 and AS93 autosamplers commercially available from PerkinElmer Health Sciences, Inc. or similar devices available from other suppliers. The OES device 1300 can be calibrated, for example, using standard concentration of elements and particles of known size to provide a calibration curve for each element which can be used to quantify each element. If desired, peak height, peak area or both can be used to determine the amount of each of the elements present in the individual particle.

In certain embodiments, the exact wavelengths of emitted light which are detected can be used to identify the particular elemental species that are present in the individual particle. Many elements can emit light at more than a single wavelength. Atomic species may also emit light at a different wavelength than ionized species. Illustrative optical emissions wavelengths for some different elemental species include, but are not limited to, 328.066 nm or 338.288 nm for silver, 396.151 nm or 308.212 nm for aluminum, 188.980 nm or 193.696 nm for arsenic, 249.772 nm or 249.676 nm for boron, 455.402 nm or 233.524 nm for barium, 313.104 nm or 313.042 nm for beryllium, 317.932 nm or 422.673 nm for calcium, 226.502 nm or 214.434 nm for cadmium, 228.615 nm or 230.785 nm for cobalt, 205.560 nm or 267.711 nm for chromium, 324.754 nm or 327.393 nm for copper, 238.201 nm or 239.568 nm for iron, 766.490 nm for potassium, 670.784 nm for lithium, 285.212 nm or 279.076 nm for magnesium, 257.607 nm or 293.305 nm manganese, 202.032 nm or 203.846 nm for molybdenum, 589.587 nm or 330.237 nm for sodium, 231.604 nm for sodium, 213.617 nm or 178.224 nm for phosphorous, 220.354 nm for lead, 180.671 nm or 181.975 nm for sulfur (as sulfate), 206.834 nm or 217.582 nm for antimony, 196.029 nm for selenium, 251.609 nm or 221.663 nm for silicon, 421.549 nm or 460.733 nm for strontium, 283.730 nm or 401.913 nm for thorium, 334.943 nm or 368.519 nm for titanium, 190.801 nm for thallium, 292.402 nm or 290.880 nm for vanadium, 409.014 nm for uranium, 207.912 nm or 239.708 nm for tungsten, 213.858 nm or 206.199 nm for zinc and 291.138 nm for lutetium. Additional suitable elemental emission wavelengths will be selected by the person of ordinary skill in the art, given the benefit of this disclosure, and depending on the detector selected, the use of radial detection, the use of axial detection, etc.

Figure 14:
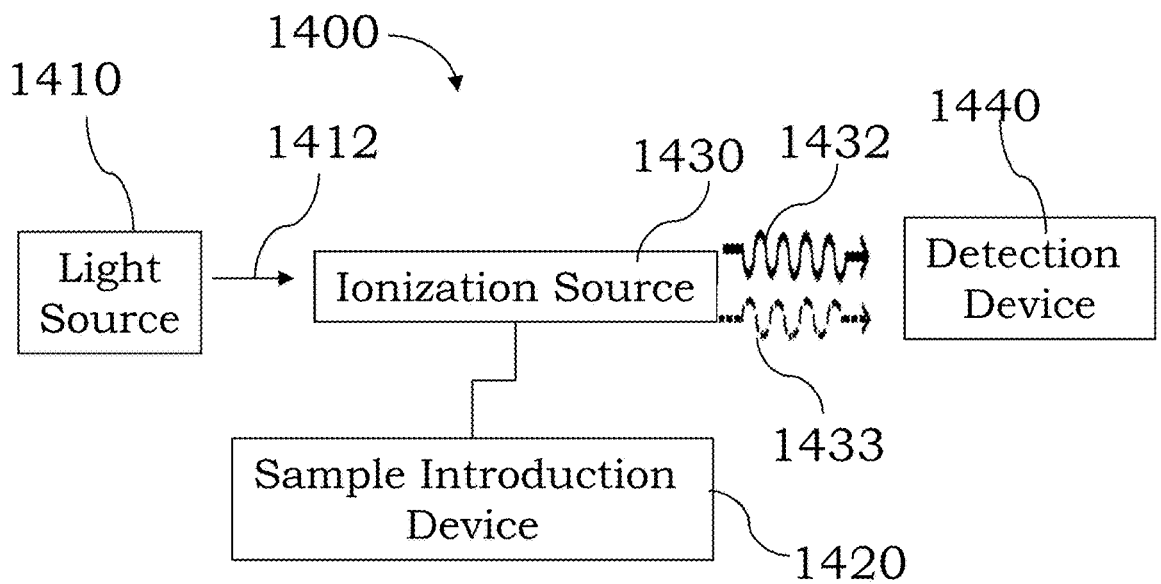
FIG. 14 is an illustration of an atomic absorption spectrometer, in accordance with certain embodiments.

In certain examples, the elemental species present in the individual particle can be detected using an atomic absorption spectrometer (AAS) to measure light absorbed by the different elemental species. Referring to FIG. 14, a single beam AAS device 1400 comprises a light source 1410, a sample introduction device 1420, an ionization device 1430, and a detection device 1440. The sample introduction device 1420 may be any one or more of those described herein or other suitable sample introduction devices. A power source (not shown) may be configured to supply power to the light source 1410, which provides one or more wavelengths of light 1412 for absorption by atoms and ions in the ionization device 1430. Suitable light sources include, but are not limited to mercury lamps, cathode ray lamps, lasers, etc. The light source 1410 may be pulsed using suitable choppers or pulsed power supplies, or in examples where a laser is implemented, the laser may be pulsed with a selected frequency, e.g. 5, 10, or 20 times/second. The exact configuration of the light source 1410 may vary. For example, the light source 1410 may provide light axially along a torch of the ionization device 1430 or may provide light radially along the torch of the ionization device 1430. The example shown in FIG. 14 is configured for axial supply of light from the light source 1410. There can be signal-to-noise advantages using axial viewing of signals. If desired, the light source can provide light to a chamber separate from the ionization device 1430, e.g. a chamber positioned downstream of the ionization device 1430. For example, the elemental species can be provided from the ionization device 1430 to a downstream chamber that is optically coupled to the light source 1410. Notwithstanding that many different configurations are possible, the detection device 1440 is optically coupled to the light source 1410 so that an amount of light absorbed by a particular elemental species is detected. In some examples, the light source 1410 can provide light of at least two different wavelengths with one wavelength being absorbed by a first elemental species and the other wavelength of light being absorbed by a second elemental species. If desired, a spectrometer can be present between the light source 1410 and the ionization device 1430 (or secondary chamber) to provide a plurality of different individual light wavelengths for absorption by the elemental species from the individual particle. The ionization device 1430 may comprise one or more components as illustrated in FIGS. 10-12 or other devices and components which can provide or sustain an ionization source. As sample is atomized and/or ionized in the ionization device 1430, the incident light 1412 from the light source 1410 may excite atoms. That is, some percentage of the light 1412 that is supplied by the light source 1410 may be absorbed by the atoms and ions in the ionization device 1430. The remaining percentage of the light may be transmitted to the detection device 1440 as wavelengths 1432, 1433. The detection device 1440 may provide one or more suitable wavelengths using, for example, prisms, lenses, gratings and other suitable devices such as those discussed above in reference to the OES devices, for example. To account for the amount of absorption by sample in the ionization device 1430, a blank, such as water or particles lacking any elemental species, may be introduced prior to sample introduction to provide a 100% transmittance reference value. The amount of light transmitted once sample is introduced into the ionization device 1430 may be measured, and the amount of light transmitted with sample may be divided by the reference value to obtain the transmittance. The negative $\log_{10}$ of the transmittance is equal to the absorbance. AAS device 1400 may further include suitable electronics such as a microprocessor and/or computer and suitable circuitry to provide a desired signal and/or for data acquisition. Suitable additional devices and circuitry may be found, for example, on commercially available AAS devices such as AAnalyst series spectrometers or PinAAcle spectrometers commercially available from PerkinElmer Health Sciences, Inc. The AAS devices may further include autosamplers known in the art, such as AS-90A, AS-90plus and AS-93plus autosamplers commercially available from PerkinElmer Health Sciences, Inc. Where the ionization device 1430 is configured to sustain an inductively coupled plasma, a radio frequency generator electrically coupled to an induction device may be present. In certain embodiments, a double beam AAS device, instead of a single beam AAS device could instead be used.

In some examples, the wavelength of light absorbed can be used to identify the elemental species present in an individual particle. Many elements may absorb light at two or more different wavelengths. In addition, atomic species may absorb different wavelength of light than ionized species. It may be desirable to select monitoring wavelengths that do not overlap one another when two or more wavelengths of light are being provided to the ionized elemental species. Further, the wavelength selected may differ when using axial detection and radial detection. Illustrative absorption wavelengths for some different elemental species include, but are not limited to, 328.1 nm for silver, 309.3 nm for aluminum, 193.7 nm for arsenic, 242.8 nm for gold, 249.7 nm for boron, 553.6 for barium, 234.9 nm for beryllium, 223.1 nm for bismuth, 422.7 nm for calcium, 228.8 nm for cadmium, 240.7 nm for cobalt, 357.9 nm for chromium, 852.1 nm for cesium, 324.8 nm for copper, 404.6 nm for dysprosium, 400.8 nm for erbium, 459.4 nm for europium, 248.3 nm for iron, 287.4 nm for gallium, 368.4 nm for gadolinium, 265.1 nm for germanium, 286.6 nm for hafnium, 253.7 nm for mercury, 410.4 nm for holmium, 303.9 nm for indium, 264.0 nm for iridium, 766.5 nm for potassium, 550 nm for lanthanum, 670.8 for lithium, 336.0 nm for lutetium, 285.2 nm for magnesium, 279.5 nm for manganese, 313.3 nm for molybdenum, 589 nm for sodium, 334.4 nm for niobium, 492.4 nm for neodymium, 232.0 nm for nickel, 290.9 nm for osmium, 213.6 nm for phosphorous, 283.3 nm for lead, 244.8 nm for palladium, 495.1 nm for praseodymium, 265.1 nm for platinum, 780.0 nm for rubidium, 346.9 nm for rhenium, 343.5 nm for rhodium, 349.9 nm for ruthenium, 217.6 nm for antimony, 391.2 nm for scandium, 196.0 nm for selenium, 251.16 nm for silicon, 429.7 nm for samarium, 286.3 nm for tin, 460.7 nm for strontium, 271.5 nm for tantalum, 432.6 nm for thorium, 261.4 nm for technetium, 214.3 nm for tellurium, 364.3 nm for titanium, 267.8 nm for thallium, 371.8 nm for thulium, 351.5 nm for uranium, 318.4 nm for vanadium, 255.1 nm for tungsten, 410.2 nm for yttrium, 398.8 nm for ytterbium, 213.9 nm for zinc, and 360.1 nm for zirconium.

In certain examples, the methods and systems herein may comprise or use a processor, which can be part of the system or instrument or present in an associated device, e.g., computer, laptop, mobile device, etc. used with the instrument. For example, the processor can be used to provide or construct an image representative of the optical emissions from the various elemental species. Such processes may be performed automatically by the processor without the need for user intervention. For example, the processor can use emission signal intensities along with one or more calibration curves to determine how much of each elemental species is present in the individual particle. In certain configurations, the processor may be present in one or more computer systems and/or common hardware circuity including, for example, a microprocessor and/or suitable software for operating the system, e.g., to control the sample introduction device, ionization device, detector, etc. In some examples, the detection device itself may comprise its own respective processor, operating system and other features to permit detection of various elemental species. The processor can be integral to the systems or may be present on one or more accessory boards, printed circuit boards or computers electrically coupled to the components of the system. The processor is typically electrically coupled to one or more memory units to receive data from the other components of the system and permit adjustment of the various system parameters as needed or desired. The processor may be part of a general-purpose computer such as those based on Unix, Intel PENTIUM-type processor, Motorola PowerPC, Sun UltraSPARC, Hewlett-Packard PA-RISC processors, or any other type of processor. One or more of any type computer system may be used according to various embodiments of the technology. Further, the system may be connected to a single computer or may be distributed among a plurality of computers attached by a communications network. It should be appreciated that other functions, including network communication, can be performed and the technology is not limited to having any particular function or set of functions. Various aspects may be implemented as specialized software executing in a general-purpose computer system. The computer system may include a processor connected to one or more memory devices, such as a disk drive, memory, or other device for storing data. Memory is typically used for storing programs, calibration curves, emission or absorption wavelengths, and data values during operation of the OES or AAS instrument. Components of the computer system may be coupled by an interconnection device, which may include one or more buses (e.g., between components that are integrated within a same machine) and/or a network (e.g., between components that reside on separate discrete machines). The interconnection device provides for communications (e.g., signals, data, instructions) to be exchanged between components of the system. The computer system typically can receive and/or issue commands within a processing time, e.g., a few milliseconds, a few microseconds or less, to permit rapid control of the system. For example, computer control can be implemented to control sample introduction, detector parameters, etc. The processor typically is electrically coupled to a power source which can, for example, be a direct current source, an alternating current source, a battery, a fuel cell or other power sources or combinations of power sources. The power source can be shared by the other components of the system. The system may also include one or more input devices, for example, a keyboard, mouse, trackball, microphone, touch screen, manual switch (e.g., override switch) and one or more output devices, for example, a printing device, display screen, speaker. In addition, the system may contain one or more communication interfaces that connect the computer system to a communication network (in addition or as an alternative to the interconnection device). The system may also include suitable circuitry to convert signals received from the various electrical devices present in the systems. Such circuitry can be present on a printed circuit board or may be present on a separate board or device that is electrically coupled to the printed circuit board through a suitable interface, e.g., a serial ATA interface, ISA interface, PCI interface or the like or through one or more wireless interfaces, e.g., Bluetooth, Wi-Fi, Near Field Communication or other wireless protocols and/or interfaces.

In certain embodiments, the storage system used in the systems described herein typically includes a computer readable and writeable nonvolatile recording medium in which codes of software can be stored that can be used by a program to be executed by the processor or information stored on or in the medium to be processed by the program. The medium may, for example, be a hard disk, solid state drive or flash memory. The program or instructions to be executed by the processor may be located locally or remotely and can be retrieved by the processor by way of an interconnection mechanism, a communication network or other means as desired. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in the storage system or in the memory system. The processor generally manipulates the data within the integrated circuit memory and then copies the data to the medium after processing is completed. A variety of mechanisms are known for managing data movement between the medium and the integrated circuit memory element and the technology is not limited thereto. The technology is also not limited to a particular memory system or storage system. In certain embodiments, the system may also include specially-programmed, special-purpose hardware, for example, an application-specific integrated circuit (ASIC) or a field programmable gate array (FPGA). Aspects of the technology may be implemented in software, hardware or firmware, or any combination thereof. Further, such methods, acts, systems, system elements and components thereof may be implemented as part of the systems described above or as an independent component. Although specific systems are described by way of example as one type of system upon which various aspects of the technology may be practiced, it should be appreciated that aspects are not limited to being implemented on the described system. Various aspects may be practiced on one or more systems having a different architecture or components. The system may comprise a general-purpose computer system that is programmable using a high-level computer programming language. The systems may be also implemented using specially programmed, special purpose hardware. In the systems, the processor is typically a commercially available processor such as the well-known Pentium class processors available from the Intel Corporation. Many other processors are also commercially available. Such a processor usually executes an operating system which may be, for example, the Windows 95, Windows 98, Windows NT, Windows 2000 (Windows ME), Windows XP, Windows Vista, Windows 7, Windows 8 or Windows 10 operating systems available from the Microsoft Corporation, MAC OS X, e.g., Snow Leopard, Lion, Mountain Lion or other versions available from Apple, the Solaris operating system available from Sun Microsystems, or UNIX or Linux operating systems available from various sources. Many other operating systems may be used, and in certain embodiments a simple set of commands or instructions may function as the operating system. Further, the processor can be designed as a quantum processor designed to perform one or more functions using one or more qubits.

In certain examples, the processor and operating system may together define a platform for which application programs in high-level programming languages may be written. It should be understood that the technology is not limited to a particular system platform, processor, operating system, or network. Also, it should be apparent to those skilled in the art, given the benefit of this disclosure, that the present technology is not limited to a specific programming language or computer system. Further, it should be appreciated that other appropriate programming languages and other appropriate systems could also be used. In certain examples, the hardware or software can be configured to implement cognitive architecture, neural networks or other suitable implementations. If desired, one or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

In some instances, various embodiments may be programmed using an object-oriented programming language, such as, for example, SQL, SmallTalk, Basic, Java, Javascript, PHP, C++, Ada, Python, iOS/Swift, Ruby on Rails or C # (C-Sharp). Other object-oriented programming languages may also be used. Alternatively, functional, scripting, and/or logical programming languages may be used. Various configurations may be implemented in a non-programmed environment (e.g., documents created in HTML, XML or other format that, when viewed in a window of a browser program, render aspects of a graphical-user interface (GUI) or perform other functions). Certain configurations may be implemented as programmed or non-programmed elements, or any combination thereof. In some instances, the systems may comprise a remote interface such as those present on a mobile device, tablet, laptop computer or other portable devices which can communicate through a wired or wireless interface and permit operation of the systems remotely as desired.

In certain examples, the processor may also comprise or have access to a database of information about elemental species and the like, which can include optical emission wavelengths, optical absorption wavelengths and other common information. For example, a collection of calibration curves for different elemental species can be stored in the database and used to estimate elemental concentrations in the individual particle without the need for the user to perform calibration curves for each of the elements. Such methods may be particularly desirable where the amount of sample is limited. The instructions stored in the memory can execute a software module or control routine for the system, which in effect can provide a controllable model of the system. The processor can use information accessed from the database together with one or software modules executed in the processor to determine control parameters or values for different components of the systems, e.g., different gas flow rates, different light wavelengths to be monitored, etc. Using input interfaces to receive control instructions and output interfaces linked to different system components in the system, the processor can perform active control over the system. For example, the processor can control the detection device, sample introduction devices, ionization devices, etc.

In some examples, the methods and systems described herein can be used to detect simultaneous optical signals from two or more different elements present in an individual particle. Quantitation of each of the elements in the individual particle introduced into the ionization device can be performed if desired. In some instances, the method comprises separating each emitted wavelength in the simultaneous optical emissions to permit detection of each elemental species over wavelength range of about 165 nm to about 790 nm and optionally to permit quantitation of an amount of each elemental species present in the individual particle.

Figures 15A, 15B:
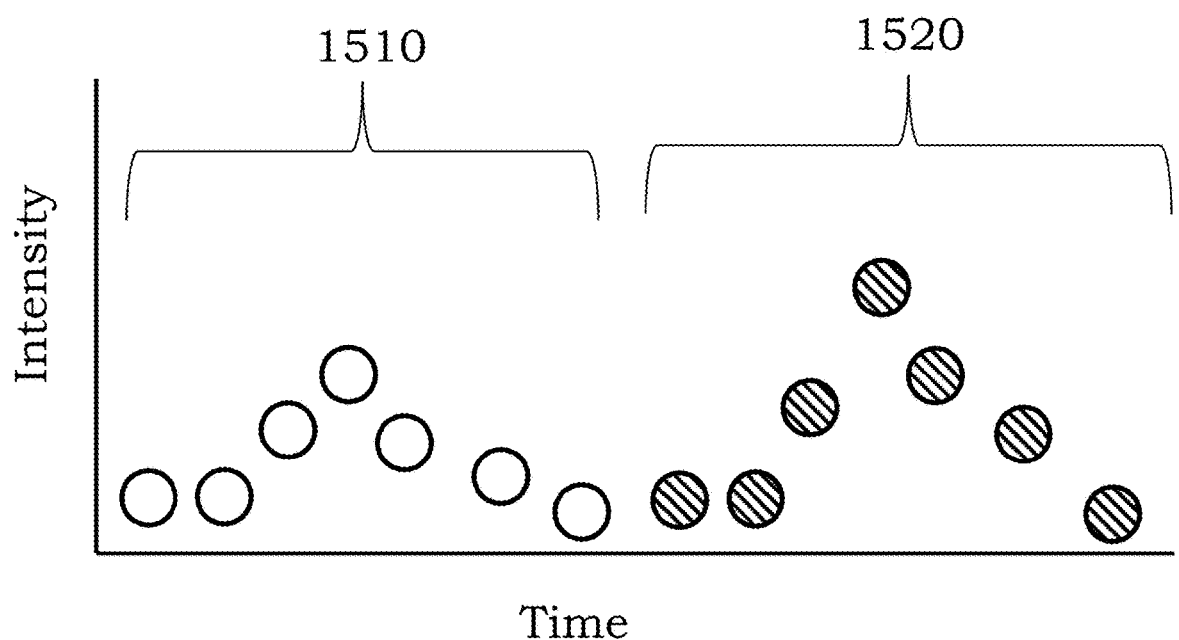
FIG. 15A is an illustration of an optical response when two different elements are present in different individual particles.
FIG. 15B shows a graph of signal intensity vs time, in accordance with certain embodiments.
Figure 16:
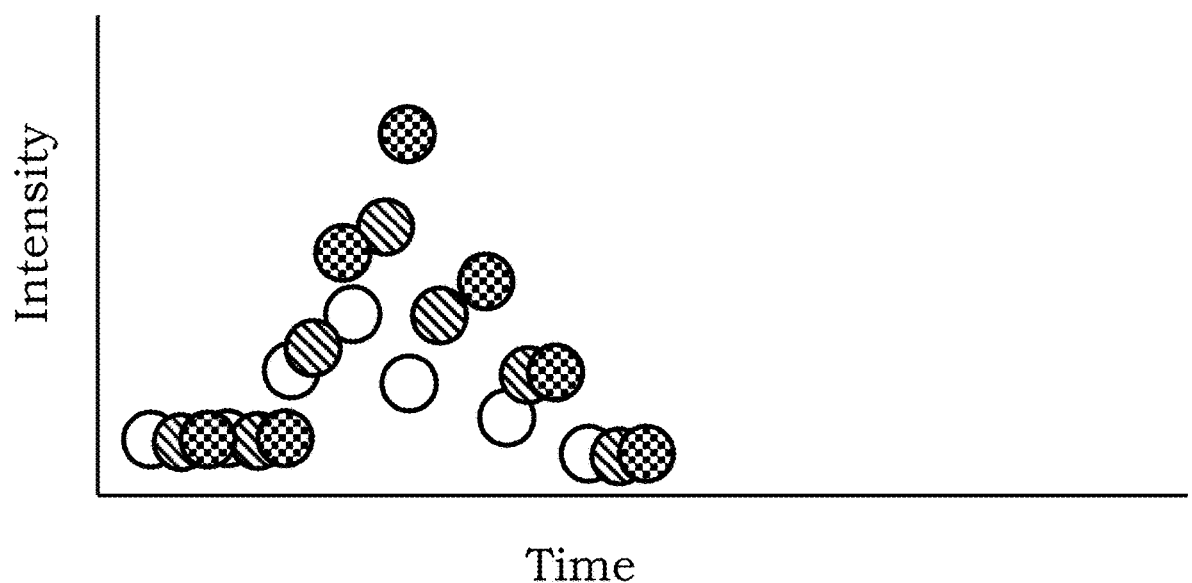
FIG. 16 is an illustration of an optical response when two different elements are present in the same individual particle, in accordance with certain embodiments.

Referring to FIG. 15A, a scenario is shown where an optical emission signal from two different elements is monitored. In this example, elements A and B are present in different particles. As the particle comprising element A arrives at the ionization source, it is ionized and emits an optical signal that can be recorded as values 1510. Element A generally emits light continuously. As the second particle comprising element B arrives at the ionization source, optical signals 1520 can be monitored. The actual emission wavelength can be used to identify the element in the particle as noted herein. Because the elements A and B are present in different particles, monitoring the signals as a function of time causes the element B signals 1520 to occur after the element A signals 1510. Even though elements A and B are present on the same graph the signals for the two elements would typically be obtained by simultaneously monitoring two different emission wavelengths. In comparison, FIG. 15B shows a graph of signal intensity vs time where elements A and B are present in the same individual particle. As the particle enters the ionization source and is ionized, both elements A and B emit simultaneously. A curve may be fit to the signals for each element to determine a curve peak height an area under the curve or both to use these values for quantifying the amount of each of elements A and B present in the individual particle. Each particle of a plurality of particles may be measured in a similar way to determine an elemental composition of each individual particle. If desired, more than two elements in any one particle may be identified and/or quantified. For example and referring to FIG. 16, a signal intensity versus time graph is shown where optical emissions from three different elements species (color coded to show the presence of different elements) are shown. A curve can be generated to the optical signals for each element and used to quantify an amount of each element present in the individual particle. Depending on the particular elements identified, the source of the particle may be traced. For example, the presence and amount of the specific elements in the individual particle can be linked back to the source of the particles. The source of the particles may be, for example, an air sample, a specific site or component in an engine or transmission, a contaminant generated during in-line production of chemicals, hydrocarbon fluids, petroleum products or other industrial materials and the like. For example, a fluid used in an inline process can be sampled periodically to monitor a state of the fluid. A first element and a second element in a particle of the sampled fluid can be identified and quantified to determine a source of the particle in the inline process. In other instances, a gas could be sampled intermittently or automatically to monitor an ambient environment of a facility.

In some examples, different particles may have similar elemental compositions which can render it difficult to determine the exact source of the particle. Use of a clustering technique for separating the particles from one source versus another due to their different elemental compositions may be performed. For example, elemental composition of different particles may be aggregated to assist in identifying the particular source of those particles and whether the source is the same or is different.

Certain specific examples are described in more detail below to facilitate a better understanding of the technology described herein.

EXAMPLE 1-ENGINE OIL ANALYSIS

A used engine oil analysis (UOA) may be performed to measure elemental species present in an individual particle. A used engine oil sample may be obtained and particulate matter can be separated from any fluids. The particular type of elements in each particle can be used to identify a wear site. For example, the presence of iron and chromium in the same particle may indicate wear of a steel component present in the engine.

EXAMPLE 2-TRANSMISSION FLUID ANALYSIS

A transmission fluid analysis may be performed to measure elemental species present in an individual particle. A sample of transmission fluid may be removed through a fill hole or through a drain, and particulate matter can be separated from any fluids. The particular type of elements can be used to identify a wear site. For example, the presence of copper and zinc the same particle may indicate wear of brass synchronizer rings of the transmission.

EXAMPLE 3-AIR MONITORING

Particulate species in air may be monitored using the techniques described herein. For example, particles of a certain size may be sampled from the air and the elements composition of each particle may be used to identify the source of the particles.

EXAMPLE 4-WATER MONITORING

A water sample may be obtained, e.g., from a well, pond, river, stream, lake, municipal feed, etc. to monitor particulate levels in the water. The particles can be separated from the water by filtration, centrifugation or other means. The elements present in each particle can be detected and identified to determine a source of the particulate matter in the water sample. For example, the identified elements can be used to trace a contaminant sample to a source.

EXAMPLE 5—INLINE SAMPLING

An inline chemical process to produce hydrocarbon fluids may be monitored by sampling particulate matter from one or more of the fluid lines. The elemental composition of each individual particle in the sampled particulate matter may be determined and used to identify a contaminant source, catalyst degradation or wear of the fluid lines in the system.

EXAMPLE 6

To test the measurement of two or more elements in a sample, a metal alloy that included lithium, manganese, nickel and chromium was analyzed using an Optima 8300 OES instrument. The levels of the four metals that were measured are shown in FIG. 17A.

Figure 17A:
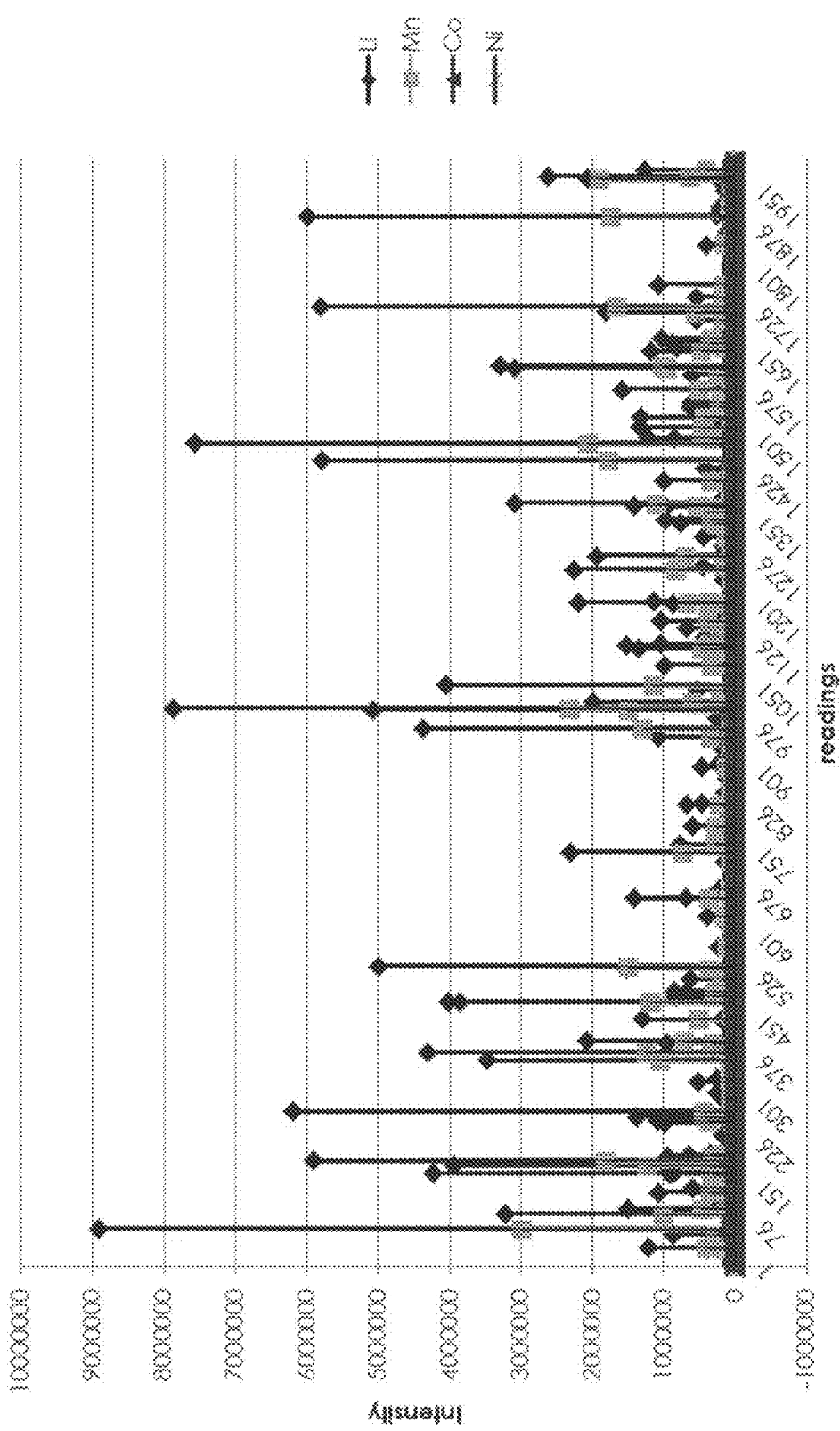
FIG. 17A is an illustration of an optical response when four different elements (lithium, manganese, cobalt and nickel) are present and measured in the sample, in accordance with certain examples.
Figure 17B:
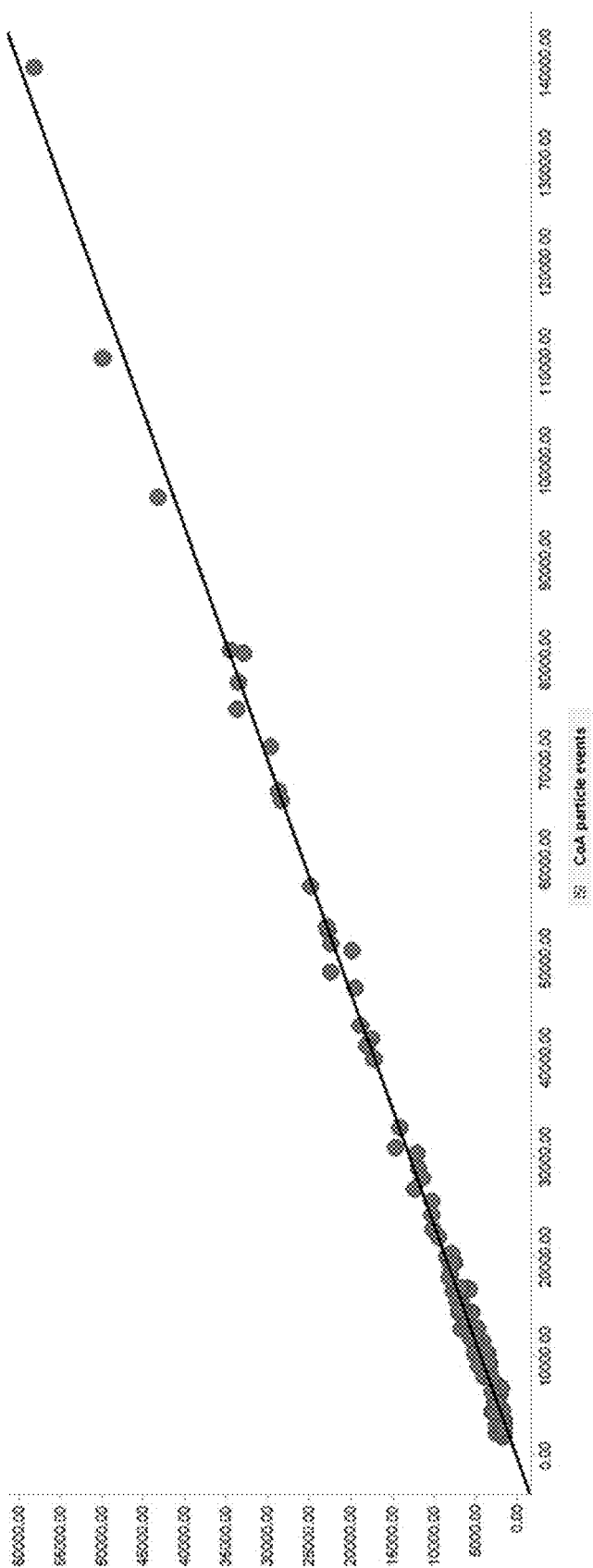
FIG. 17B shows a simulation where the nickel and cobalt are present in the same particle, in accordance with some examples.

Several possible scenarios may exist for the metals measured in FIG. 17A. Referring to FIG. 17B, a Spotfire analysis and linear regression is shown assuming that the nickel and cobalt coexist in the same particles. The graph of FIG. 17B includes cobalt particle events on the x-axis and nickel particle events on the y-axis. There is a highly linear response which is indicative of the metals being present in the sample particle.

Figure 17C:
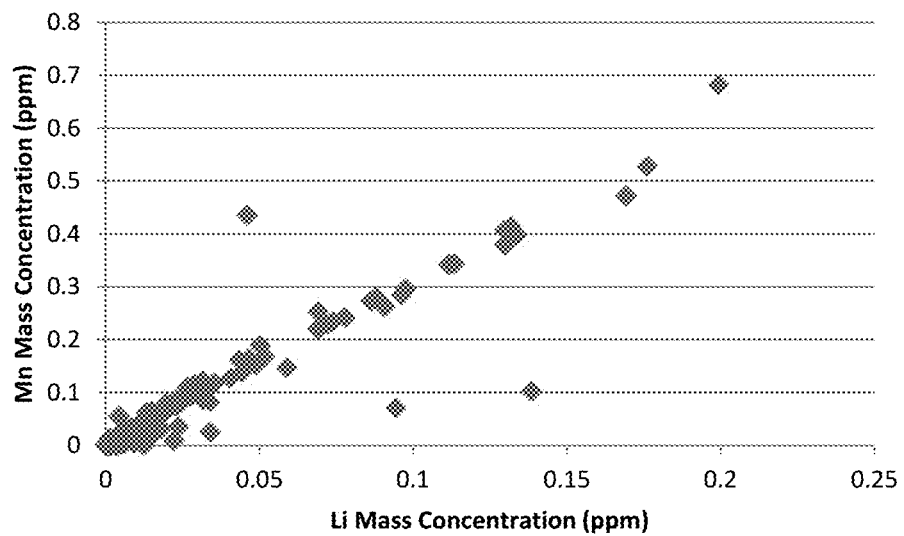
FIGS. 17C, 17D, 17E, 17F, 17G and 17H show various graphs correlating different metal measurements with each other, in accordance with certain embodiments.
Figure 17D:
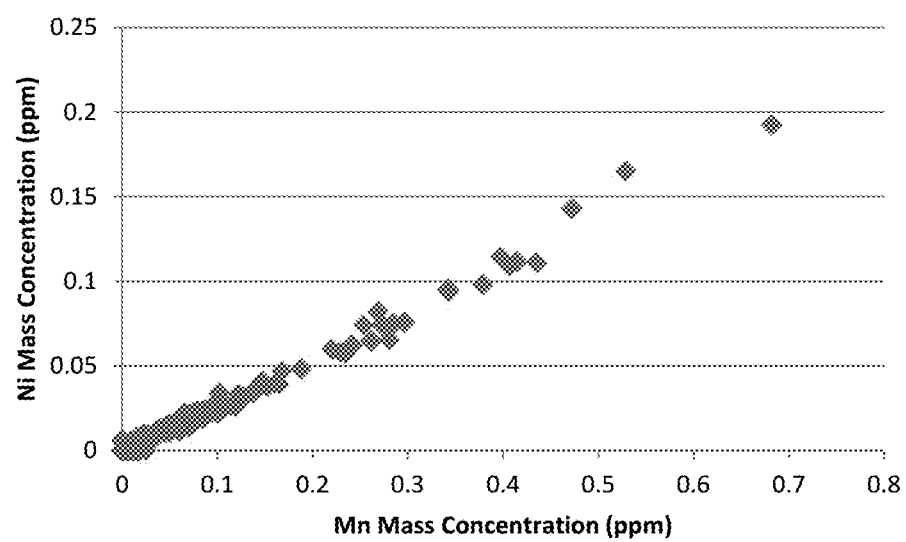
Figure 17E:
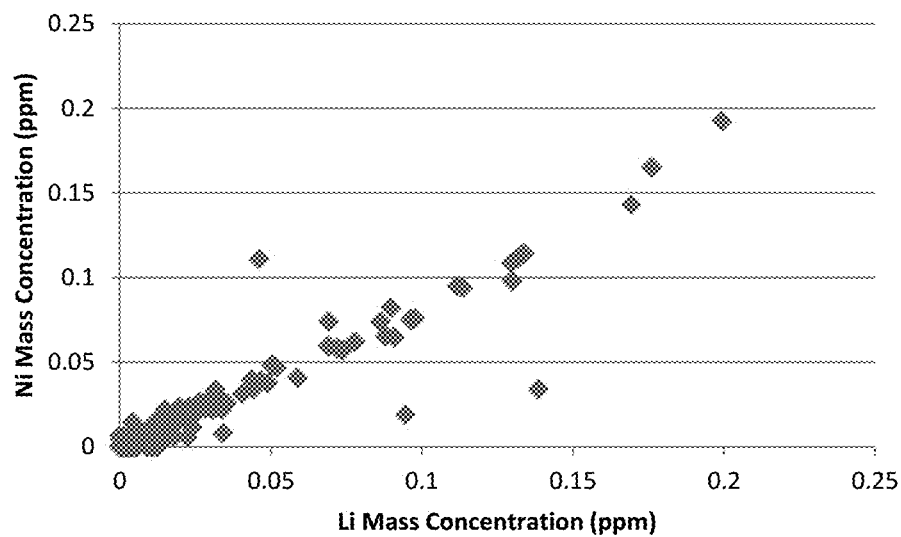
Figure 17F:
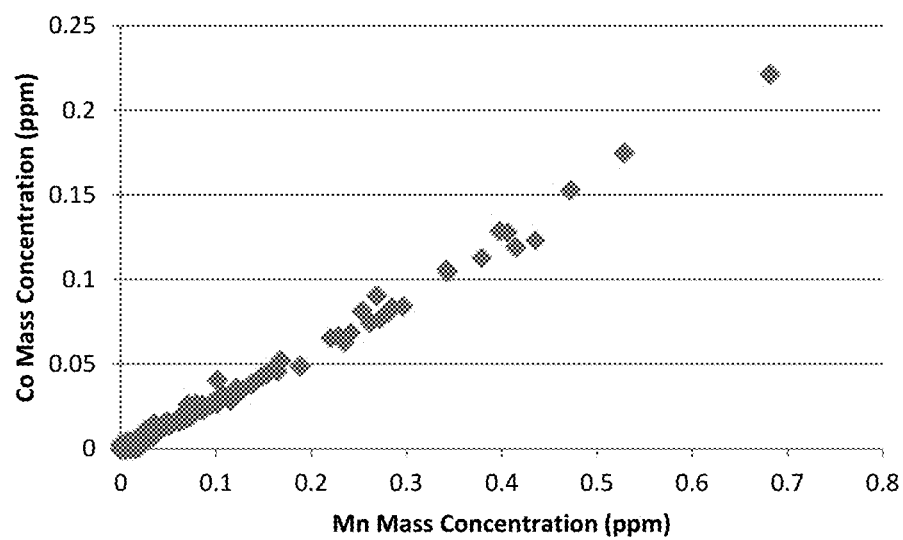
Figure 17G:
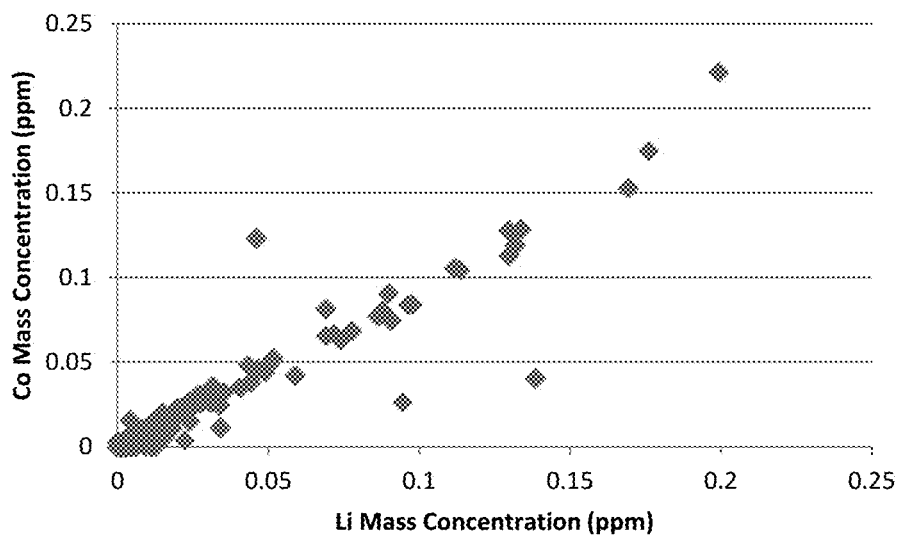
Figure 17H:
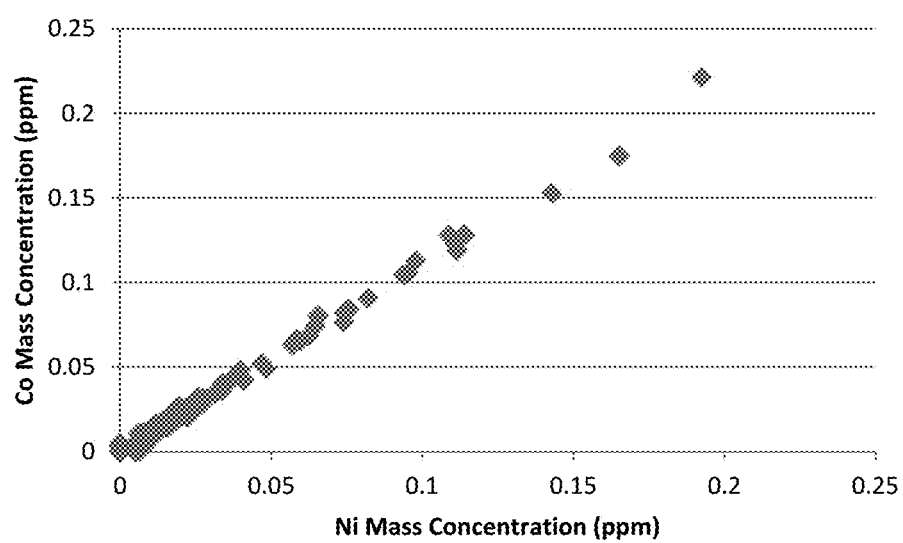

FIGS. 17C-17H show graphs were different pair of metals are correlated. FIG. 17C shows correlation of manganese (y-axis) and lithium (x-axis). FIG. 17D shows correlation of nickel (y-axis) and manganese (x-axis). FIG. 17E shows correlation of nickel (y-axis) and lithium (x-axis). FIG. 17F shows correlation of cobalt (y-axis) and manganese (x-axis). FIG. 17G shows correlation of cobalt (y-axis) and lithium (x-axis). FIG. 17H shows correlation of cobalt (y-axis) and nickel (x-axis). The various curves can be used to better understand whether two, three or all four of the metals are present in the same particle.

EXAMPLE 7

A used engine oil sample was analyzed using an Optima 8300 OES instrument to measure the levels of iron and chromium to confirm the presence of steel in the used engine oil. The results are shown in FIGS. 18A-18E. FIGS. 18A and 18C shows the signal intensities for iron as a function of time. FIGS. 18B, 18D and 18E show the signal intensities for chromium as a function of time. Both iron and chromium were observed confirming the presence of steel in the used engine oil sample.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A method comprising:
ionizing a sample comprising a plurality of particles, wherein the plurality of particles comprise a particle comprising a first element and a second element, and wherein ionization of the sample provides excited, ionized first element and excited, ionized second element;
simultaneously detecting a wavelength of an optical emission from each of the excited, ionized first element and the excited, ionized second element to identify at least the first element in the particle from the plurality of particles using the optical emission from the excited, ionized first element, and to identify at least the second element in the particle from the plurality of particles using the optical emission from the excited, ionized second element; and
using the identified first element and the identified second element to identify a source of the particle.

2. The method of claim 1, further comprising quantifying an amount of each of the first element and the second element in the particle.

3. The method of claim 1, further comprising simultaneously detecting an optical emission from an excited, ionized third element to identify a third element in the particle using the optical emission from the excited, ionized third element and identifying the source of the particle using the identified first, second and third elements.

4. The method of claim 3, further comprising quantifying an amount of each of the first element, the second element and the third element in the particle.

5. The method of claim 1, further comprising sampling air comprising the particle and providing the sampled air to an ionization device to ionize the first element and the second element in the sampled air.

6. The method of claim 1, further comprising sampling a hydrocarbon fluid comprising the particle and providing the sampled hydrocarbon fluid to an ionization device to ionize the first element and the second element in the sampled hydrocarbon fluid.

7. The method of claim 6, further comprising quantifying an amount of each of the first element and the second element in the particle and determining a vehicle site exhibiting wear using the quantified amount of the first element and the second element.

8. The method of claim 6, further comprising quantifying an amount of each of the first element and the second element in the particle and determining if the hydrocarbon fluid needs to be replaced using the quantified amount of the first element and the second element.

9. The method of claim 1, further comprising simultaneously detecting an optical emission from each excited, ionized element from all elements in the particle to identify all elements in the particle.

10. The method of claim 9, further comprising quantifying each of the identified elements in the particle and determining a source of the particle using the quantified elements.

11. The method of claim 1, further comprising configuring the particle as a nanoparticle.

12. The method of claim 11, further comprising identifying the source of the nanoparticle using the identified first element and the identified second element.

13. The method of claim 1, wherein the ionizing the sample comprises introducing the plurality of particles into an ionization source.

14. The method of claim 13, further comprising introducing the plurality of particles into the ionization source using a spray chamber.

15. The method of claim 13, further comprising configuring the ionization source as one of an inductively coupled plasma, a capacitively coupled plasma, a glow discharge, an arc or a spark.

16. The method of claim 1, further comprising sampling a fluid comprising the particle, wherein the fluid is sampled in an inline process to monitor a state of the fluid by periodically sampling the fluid, identifying the first element and the second element in the sampled fluid using the optical emissions from the excited, first ionized element and the excited, second ionized element, and quantifying an amount of each of the first element and the second element in the sampled fluid to determine a source of the particle in the inline process.

17. The method of claim 16, further comprising sampling a gas comprising the plurality of particles.

18. The method of claim 16, further comprising sampling a gas used in a semiconductor manufacturing process.

19. The method of claim 1, wherein each of the first element and the second element are inorganic elements.

20. The method of claim 1, further comprising selecting the sample from one or more of an air sample, a specific site of an engine, a specific component of an engine, a specific site of a transmission, a specific component of a transmission, a contaminant generated during production of chemicals, a contaminant generated during production of hydrocarbons, a contaminant generated during production of petroleum products, or a contaminant generated during production of industrial materials.

* * * * *